United States Patent
May et al.

(10) Patent No.: US 11,471,194 B2
(45) Date of Patent: Oct. 18, 2022

(54) POP-ON-CAP ASSEMBLIES HAVING OPPOSING SPLAY-RESISTING FEATURES AND GENERALLY RECTANGULAR OPPOSING ROTATION-PREVENTING/ ROTATION-RESISTING FEATURES FOR SPINAL SURGERY

(71) Applicant: Warsaw Orthopedic, Inc., Warsaw, IN (US)

(72) Inventors: Jason M. May, St. Johns, FL (US);
Christel Italiaie, Memphis, TN (US);
William Rezach, Covington, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 16/835,748

(22) Filed: Mar. 31, 2020

(65) Prior Publication Data
US 2021/0298800 A1    Sep. 30, 2021

(51) Int. Cl.
*A61B 17/70*    (2006.01)
*A61B 17/86*    (2006.01)

(52) U.S. Cl.
CPC ...... *A61B 17/7037* (2013.01); *A61B 17/7091* (2013.01); *A61B 17/8665* (2013.01)

(58) Field of Classification Search
CPC .......... A61B 17/7032–17/704; A61B 17/8685; A61B 17/8665–2017/868
See application file for complete search history.

(56) References Cited

U.S. PATENT DOCUMENTS 10,383,675 B1    8/2019    Cummins et al.
2006/0200128 A1*    9/2006    Mueller ............. A61B 17/7037
                                                        606/308

(Continued)

FOREIGN PATENT DOCUMENTS

WO    2004032726 A2    4/2004

OTHER PUBLICATIONS

European Patent Office, 80298 Munich Germany, European Search Report, Application No. 151315.5-1 132, Applicant: Warsaw Orthopedic, Inc., dated Jun. 16, 2021.

*Primary Examiner* — Julianna N Harvey
(74) *Attorney, Agent, or Firm* — Sorell, Lenna & Schmidt, LLP

(57) ABSTRACT

A spinal-surgery system having a rod receiver and/or a cap having a generally cylindrical body, a set of opposing splay-resisting flanges, and a set of opposing rotation-preventing/rotation-resisting wings. Each wing has a lateral rotation-preventing portion and a lateral rotation-resisting portion. A receiver proximal end forms a wing-receiving cavity having a lateral rotation-preventing side and a lateral rotation-resisting side. Each flange has a proximal-facing splay-resist surface, and a distal-facing pop-on surface. Each receiver proximal protrusion has a proximal-facing sloped receiver pop-on surface, and a distal-facing sloped receiver splay-resist surface. Each rotation-preventing portion contacts a corresponding rotation-preventing side and each rotation-resisting portion contacts a corresponding rotation-resisting sides when the cap is popped on. The rotation-preventing portions contacting the rotation-preventing sides prevents cap rotation in a first direction. The rotation-resisting portion contacting the rotation-resisting side resists cap rotation in a second direction, but allows rotation in the second, forcing the arms to splay.

28 Claims, 11 Drawing Sheets

(56) References Cited

U.S. PATENT DOCUMENTS

| | | | |
|---|---|---|---|
| 2009/0062866 A1* | 3/2009 | Jackson | A61B 17/86 606/301 |
| 2014/0081334 A1* | 3/2014 | Jackson | A61B 17/683 606/278 |
| 2016/0296266 A1 | 10/2016 | Chandanson et al. | |
| 2016/0338742 A1* | 11/2016 | Peterson | A61B 17/7037 |
| 2018/0243022 A1 | 8/2018 | Marek et al. | |
| 2019/0247094 A1* | 8/2019 | Yacoub | A61B 17/7035 |

* cited by examiner

POP-ON-CAP ASSEMBLIES HAVING
OPPOSING SPLAY-RESISTING FEATURES
AND GENERALLY RECTANGULAR
OPPOSING ROTATION-PREVENTING/
ROTATION-RESISTING FEATURES FOR
SPINAL SURGERY

FIELD

The present disclosure relates to implants for use in spinal surgeries generally and, more particularly to spinal systems including pop-on cap implants and the corresponding receivers, wherein the caps and receivers are configured such that (i) the caps can be popped on by intentionally splaying receiver arms, (ii) the cap interfaces with the receiver after being popped on to resist receiver-arm splay, and (iii) the caps can later, for revision procedures, be removed readily from the receivers, by intentionally splaying receiver arms.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders.

Surgical treatment of these spinal disorders includes correction, fusion, fixation, discectomy, laminectomy and implantable prosthetics.

Surgical rods are used commonly in correcting spinal abnormalities. Pedicle-screw assemblies are often used to facilitate securement of one or more spinal rods relative to the spine. Pedicle-screw assemblies include a bonescrew attached to a rod-receiving receiver. The bonescrews are attached to patient vertebrae, and the receivers receive portions of the spinal rod.

Receivers typically have opposing arms extending proximally from a distal base, forming a rod-receiving cavity between them. The arms often undesirably splay away from each other during locking of the receiver to the rod. Various prior methods have been used to prevent or limit this splay.

Another need relates to the occasional need to revise a previously implanted construct. Removing set-screws, to release or adjust the rod for these procedures, can be difficult.

SUMMARY

Systems and processes of the present disclosure relate generally to implants for use in spinal surgeries and, more particularly, to systems having cap implants configured to (i) pop by fully distal motion onto corresponding rod receivers, (ii) prevent splay of receiver arms when installed, and (ii) be removed readily from the receivers in potential revision surgeries.

In one aspect, the present disclosure provides a system for use in spinal surgery, including a cap having a generally cylindrical body, a set of opposing splay-resisting flanges extending radially from the body, and a set of opposing rotation-preventing/rotation-resisting wings extending radially from the body, each cap wing having a lateral rotation-preventing portion and a lateral rotation-resisting portion. The system also includes a receiver having opposing arms spaced equally from a longitudinal axis of the receiver, each arm extending to a respective proximal end from a common distal base and having an inner proximal protrusion at or adjacent the proximal end, the proximal end forming a wing-receiving cavity having a lateral rotation-preventing side and a lateral rotation-resisting side. Each cap flange has a proximal-facing splay-resist surface, sloped proximally and radially outward, and a distal-facing pop-on surface. Each receiver proximal protrusion has (i) a proximal-facing sloped receiver pop-on surface extending distally and radially inward toward the longitudinal axis, and (ii) a distal-facing sloped receiver splay-resist surface extending distally and radially inward toward the longitudinal axis. Each rotation-preventing portion contacts a corresponding one of the rotation-preventing side and each rotation-resisting portion contacts a corresponding one of the rotation-resisting sides when the cap is popped onto the receiver. The rotation-preventing portions and rotation-preventing sides are configured such that when the cap is installed onto the receiver, the rotation-preventing portions contacting the rotation-preventing sides prevents cap rotation in a first direction. The rotation-resisting portion and rotation-resisting side are configured such that when the cap is installed onto the receiver, the rotation-resisting portion contacting the rotation-resisting side resists cap rotation in a second direction, opposite the first direction, but allows cap rotation in the second direction in response to a threshold torque being applied to the cap in the second direction. The rotation-resisting portions force the arms to splay when the cap is rotated by at least the threshold torque in the second direction in use of the system.

In some cases, each rotation-preventing/rotation-resisting wing has a generally rectangular profile, looking distally at the cap.

Each rotation-preventing/rotation-resisting wing has opposing wing sides, each side extending from the body at a wing-cap interface generally orthogonally to a tangent of the body at or adjacent the interface.

Each cap rotation-preventing portion has a rotation-resisting portion extending from the cap body at a wing base, and each cap rotation-preventing portion extends from the wing base at an angle, with respect to a body tangent contacting an edge of the wing base, of between about 80 degrees and about 100 degrees.

Each cap rotation-preventing portion has a rotation-resisting portion extending from the cap body at a wing base, and each cap rotation-resisting portion extends from the wing base at an angle, with respect to a body tangent contacting an edge of the wing base, of between about 80 degrees and about 100 degrees.

Each arm has a curved rim, and each receiver rotation-preventing side extends at an angle, with respect to respective a rim tangent, of between about 80 degrees and about 100 degrees.

The flanges extend radially from the body along a first radial line of the body, and the wings extend radially away from the body along a second radial line of the body generally orthogonal to the first radial line.

The flanges are distal to the wings.

The flanges extend from the body along a first radial line of the body. And the wings extend radially from the body along a second radial line of the body generally parallel to the first radial line.

Proximal surfaces of the cap wings lie on a first plane, and proximal surfaces of the receiver arms lie on a second plane distal to the first plane when the cap is popped onto the receiver.

The receiver pop-on surfaces are spaced from each other such that each cap pop-on surface contacts a respective one of the receiver pop-on surfaces when the cap is centered on the longitudinal axis, with the cap wings aligned over the wing-receiving cavities, and moved distally to contact the receiver.

Each receiver pop-on surface extends at a receiver pop-on angle with respect to a horizontal reference frame of between about 50 degrees and about 80 degrees.

Each receiver arm has an inner surface extending from a distal portion to a proximal portion adjacent said proximal end of the arm, and the proximal portion of each inner surface defines a protrusion cavity configured to receive the cap flange when the cap is popped onto the receiver.

The proximal end of each receiver arm has opposing side areas, each cap wing extends between a first side end and a second side end, and the rotation-preventing portion of each cap wing is at the first side end of the cap wing. Further, a first side area of the opposing receiver-arm side areas has the rotation-preventing side of the receiver, for abutting the rotation-preventing portion of the cap wing when the cap is installed into the receiver, preventing relative rotation of the cap in the first direction with respect to the receiver when the cap is installed into the receiver, and a second side area of the opposing receiver-arm side areas is generally open, such that the cap wing is not impeded from rotating in the second direction at the second side area on a second side of the wing when the cap is installed into the receiver.

In another aspect, the present disclosure provides a system for use in spinal surgery, having a cap configured to be popped into a rod receiver, the cap having a generally cylindrical body, a set of opposing splay-resisting flanges extending radially from the body, and a set of opposing rotation-preventing/rotation-resisting wings extending radially from the body, each cap wing having a lateral rotation-preventing portion and a lateral rotation-resisting portion. The receiver has opposing arms spaced equally from a longitudinal axis of the receiver, each arm extending to a respective proximal end from a common distal base and having an inner proximal protrusion at or adjacent the proximal end, the proximal end forming a wing-receiving cavity having a lateral rotation-preventing side and a lateral rotation-resisting side, each receiver proximal protrusion having (i) a proximal-facing sloped receiver pop-on surface extending distally and radially inward toward the longitudinal axis, and (ii) a distal-facing sloped receiver splay-resist surface extending distally and radially inward toward the longitudinal axis. Each cap flange has a proximal-facing splay-resist surface, sloped proximally and radially outward, and a distal-facing pop-on surface. Each rotation-preventing portion contacts a corresponding one of the rotation-preventing side and each rotation-resisting portion contacts a corresponding one of the rotation-resisting sides when the cap is popped onto the receiver. The rotation-preventing portions of the cap are configured such that when the cap is installed onto the receiver, the rotation-preventing portions contacting the rotation-preventing sides prevents cap rotation in a first direction. The rotation-resisting portions of the cap are configured such that when the cap is installed onto the receiver, the rotation-resisting portion contacting the rotation-resisting side resists cap rotation in a second direction, opposite the first direction, but allows cap rotation in the second direction in response to a threshold torque being applied in the second direction to the cap. The rotation-resisting portions of the cap are configured to force the arms to splay when the cap is rotated by at least the threshold torque in the second direction in use of the system.

Each rotation-preventing/rotation-resisting wing has a generally rectangular profile, looking distally at the cap.

Each rotation-preventing/rotation-resisting wing has opposing wing sides, each side extending from the body at a wing-cap interface generally orthogonally to a tangent of the body at or adjacent the interface.

Each cap rotation-preventing portion has a rotation-resisting portion extending from the cap body at a wing base. Each cap rotation-preventing portion extends from the wing base at an angle, with respect to a body tangent contacting an edge of the wing base, of between about 80 degrees and about 100 degrees.

Each cap rotation-preventing portion has a rotation-resisting portion extending from the cap body at a wing base, and each cap rotation-resisting portion extends from the wing base at an angle, with respect to a body tangent contacting an edge of the wing base, of between about 80 degrees and about 100 degrees.

Each arm has a curved rim, and each receiver rotation-preventing side extends at an angle, with respect to respective a rim tangent, of between about 80 degrees and about 100 degrees.

The flanges extend radially from the body along a first radial line of the body, and the wings extend radially away from the body along a second radial line of the body generally orthogonal to the first radial line The flanges are distal to the wings.

The flanges extend from the body along a first radial line of the body, and the wings extend radially from the body along a second radial line of the body generally parallel to the first radial line.

Proximal surfaces of the cap wings lie on a first plane, and proximal surfaces of the receiver arms lie on a second plane distal to the first plane when the cap is popped onto the receiver.

In yet another aspect, the present disclosure provides a system for use in spinal surgery, including a receiver configured to receive a pop-on cap, the receiver having opposing arms spaced equally from a longitudinal axis of the receiver, each arm extending to a respective proximal end from a common distal base and having an inner proximal protrusion at or adjacent the proximal end, the proximal end forming a wing-receiving cavity having a lateral rotation-preventing side and a lateral rotation-resisting side. The cap has a generally cylindrical body, a set of opposing splay-resisting flanges extending radially from the body, and a set of opposing rotation-preventing/rotation-resisting wings extending radially from the body, each cap wing having a lateral rotation-preventing portion and a lateral rotation-resisting portion, each cap flange having a proximal-facing splay-resist surface, sloped proximally and radially outward, and a distal-facing pop-on surface, each receiver proximal protrusion having (i) a proximal-facing sloped receiver pop-on surface extending distally and radially inward toward the longitudinal axis, and (ii) a distal-facing sloped receiver splay-resist portion extending distally and radially inward toward the longitudinal axis, and each rotation-preventing portion contacting a corresponding one of the rotation-preventing side and each rotation-resisting portion contacts a corresponding one of the rotation-resisting sides when the cap is popped onto the receiver. The rotation-preventing sides of the receiver are configured such that when the cap is installed onto the receiver, the rotation-preventing portions contacting the rotation-preventing sides prevents cap rotation in a first direction. The rotation-resisting sides of the receiver are configured such that when the cap is installed onto the receiver, the rotation-resisting portions contacting the rotation-resisting sides resists cap rotation in a second direction, opposite the first direction, but allows cap rotation in the second direction in response to a threshold torque being applied to the cap in the second direction. The rotation-resisting sides of the receiver are configured such that force from the rotation-resisting portions cause the sides to splay when the cap is rotated by at least the threshold torque in the second direction in use of the system.

Each arm has a curved rim, and each receiver rotation-preventing side extends at an angle, with respect to a respective rim tangent, of between about 80 degrees and about 100 degrees.

The proximal end of each receiver arm has opposing or adjacent side areas, each cap wing extends between a first side end and a second side end, and the rotation-preventing portion of each cap wing is at the first side end of the cap wing. Also, a first side area of the opposing receiver-arm side areas has the rotation-preventing side of the receiver, for abutting the rotation-preventing portion of the cap wing when the cap is installed into the receiver, preventing relative rotation of the cap in the first direction with respect to the receiver when the cap is installed into the receiver, and a second side area of the opposing receiver-arm side areas is generally open, such that the cap wing is not impeded from rotating in the second direction at the second side area on a second side of the wing when the cap is installed into the receiver.

The receiver pop-on surfaces are spaced from each other such that each cap pop-on surface contacts a respective one of the receiver pop-on surfaces when the cap is centered on the longitudinal axis, with the cap wings aligned over the wing-receiving cavities, and moved distally to contact the receiver.

Each receiver pop-on surface extends at a receiver pop-on angle with respect to a horizontal reference frame of between about 50 degrees and about 80 degrees.

Each receiver arm has an inner surface extending from a distal portion to a proximal portion adjacent said proximal end of the arm, and the proximal portion of each inner surface defines a protrusion cavity configured to receive the cap flange when the cap is popped onto the receiver.

Details of various aspects of the disclosure are set forth in the accompanying drawings and description below. Other features, objects, and advantages of the technology will be apparent from the description, drawings, and claims.

BRIEF DESCRIPTION OF DRAWINGS

FIG. 4 is a perspective view showing the cap contacting the receiver, prior to being popped on;

DETAILED DESCRIPTION

The present description presents three primary embodiments, each having related features and including various sub-embodiments. Each of the embodiments relate to systems including surgical caps configured to (i) pop onto a rod receiver, (ii) lock into the receiver to resist receiver arm splay, and (ii) be removed selectively from the receiver, by user application of a relatively low torque or force, and to the corresponding receiver configured to facilitate the same. Embodiments also describe instruments used to effect these maneuvers.

Figure 1:
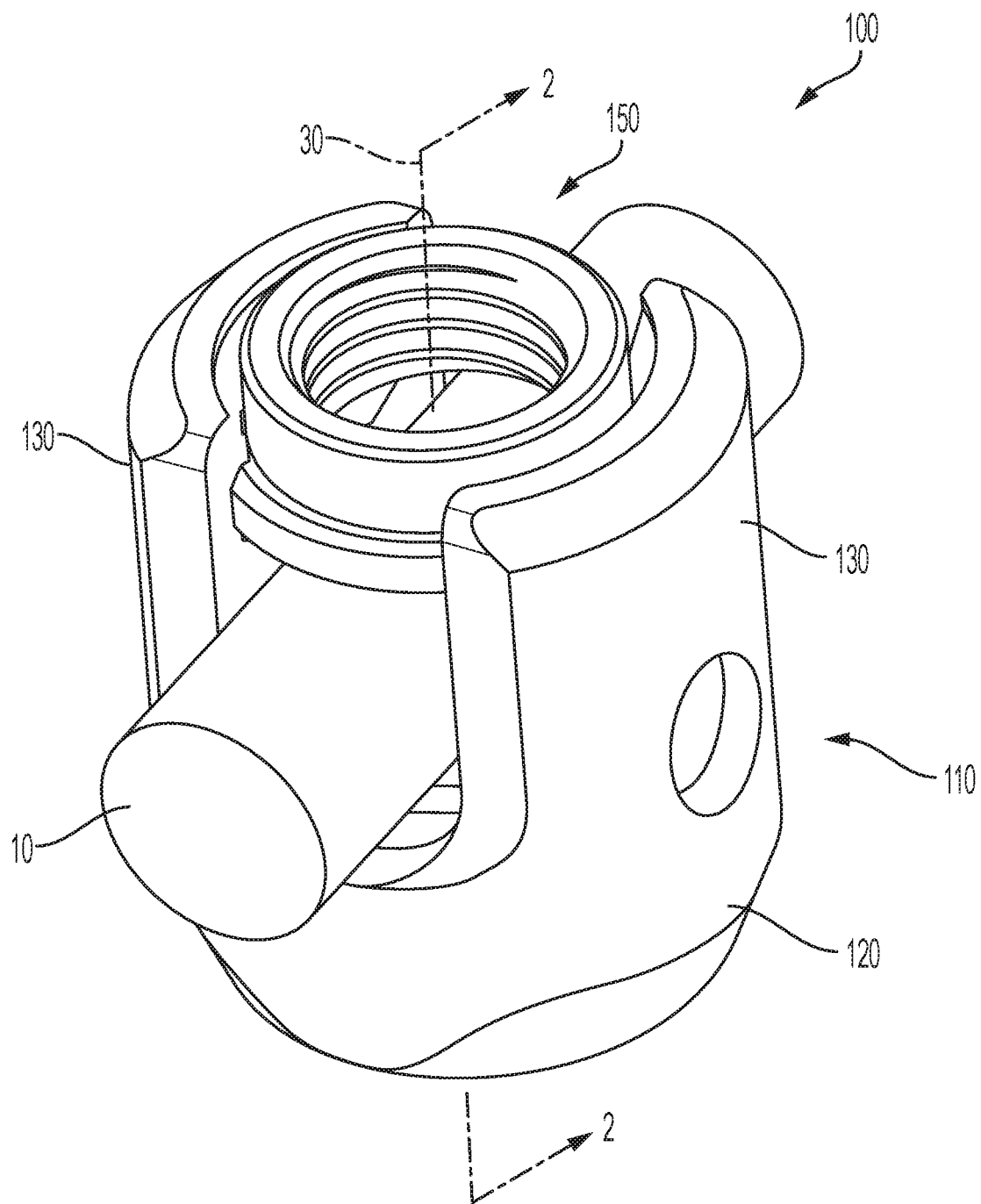
FIG. 1 is a perspective view of a cap and receiver system, according to a first embodiment of the present technology.

Turning now to the drawings, and more particularly to the first figure, FIG. 1 shows a perspective view of a first embodiment of a cap and receiver system, indicated generally by reference numeral 100.

The system 100 includes a receiver implant 110 and a corresponding cap implant 150. The receiver 110 can be referred to by various terms, such as tulip or screw head. The receiver 110 and cap 150 have corresponding geometries, for mating together by popping the cap 150 onto the receiver 110. The cap is popped onto the receiver 110 by fully-distally-directed motion of the cap 150, along a longitudinal (proximal-to-distal) axis 30 of the receiver, down onto the receiver 110.

The receiver 110 has opposing arms 130 extending proximally from a distal base 120. The base 120 is configured for receiving or being connected to a bone screw (not shown) for anchoring the system 100 to a patient vertebra. The opposing receiver arms 130 define a rod-receiving cavity between them. A rod 10 is shown positioned in the cavity. The rod 10 can be considered a part of the system 100, or used with it.

Figure 2:
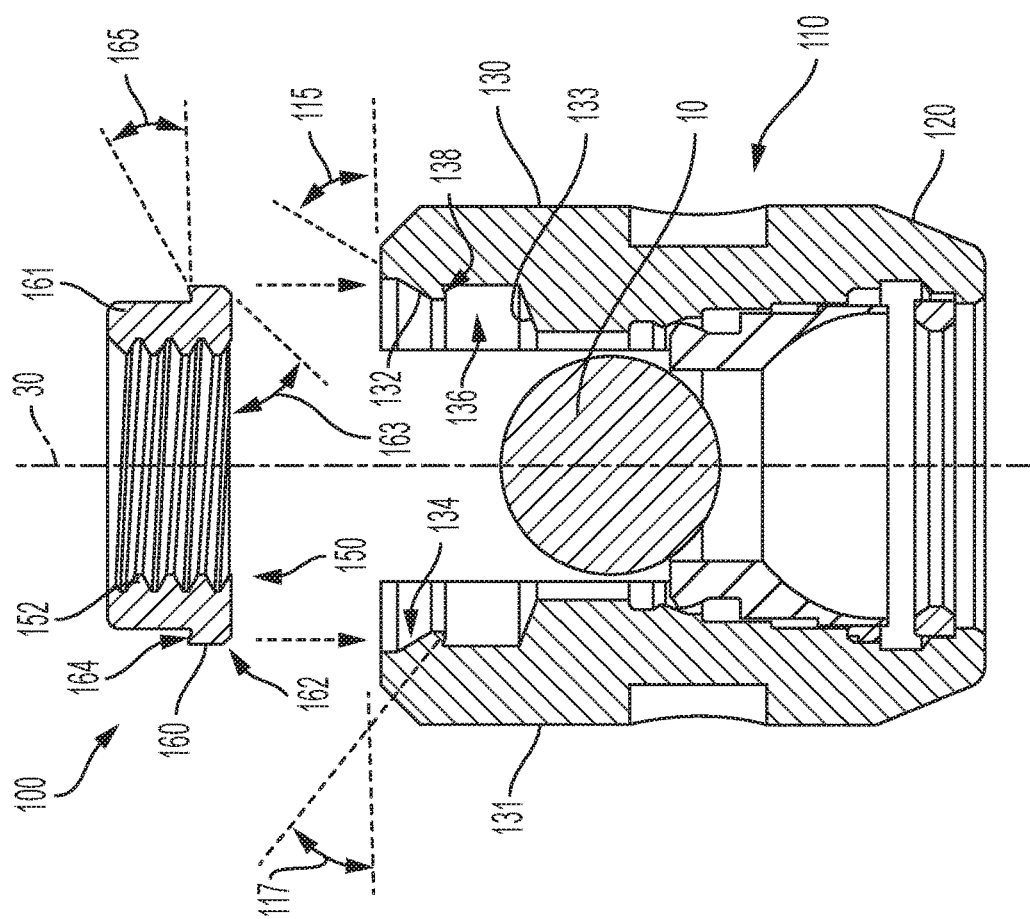
FIG. 2 is a side cross section of the system taken along line 2-2 of FIG. 1, showing the cap being lowered onto the receiver.

FIG. 2 is a side cross section of the system 100 taken along line 2-2 of FIG. 1, showing the cap 150 being lowered onto the receiver 110.

The cap 150 has an internal thread 152 for receiving a setscrew in operation of the system 100. The setscrew can be loaded before or after the cap 150 is popped into the receiver

Figure 12:
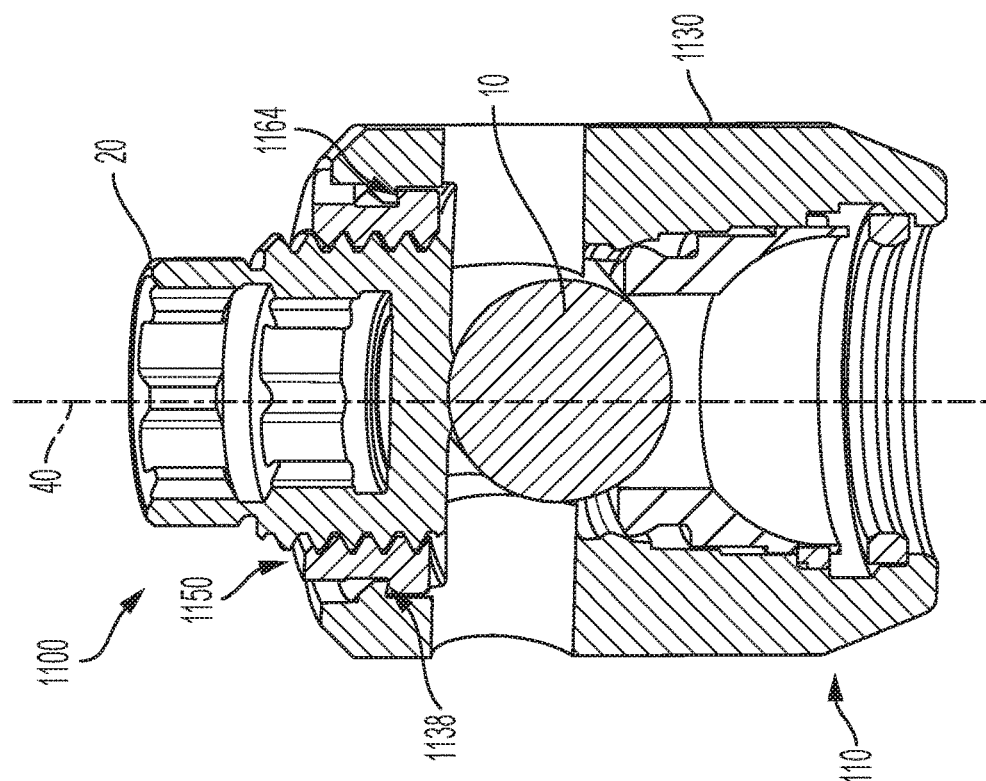
FIG. 12 is a side cross section of the system of the third embodiment, taken along line 12 of FIG. 11, having a setscrew threaded into the cap.
Figure 14:
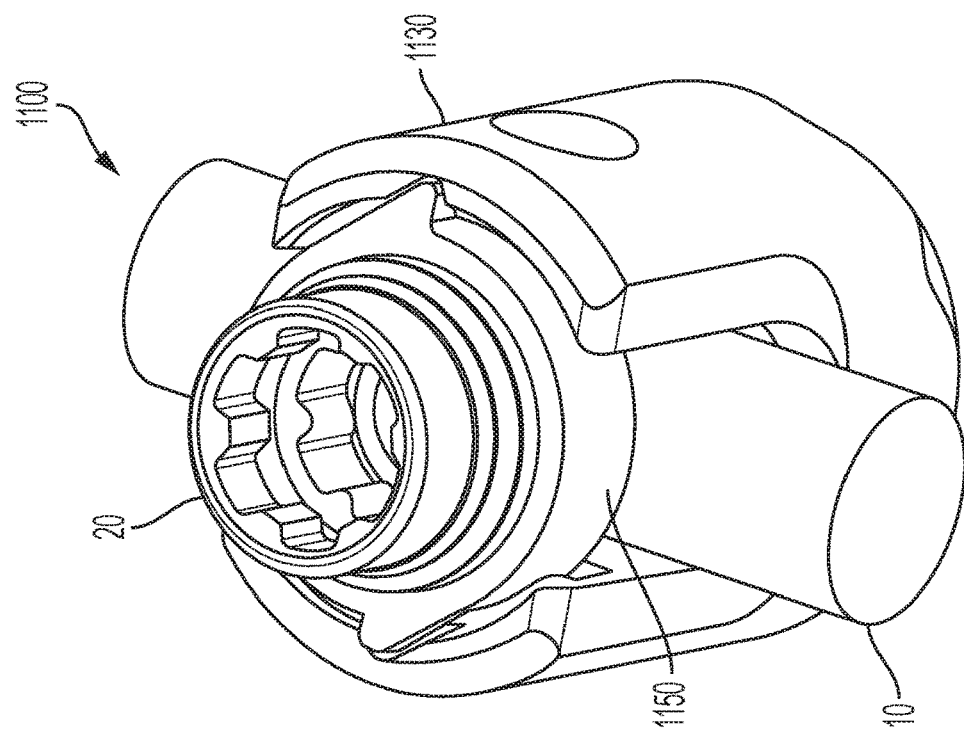
FIG. 14 is a perspective view of the arrangement of FIGS. 12 and 13.
Figure 13:
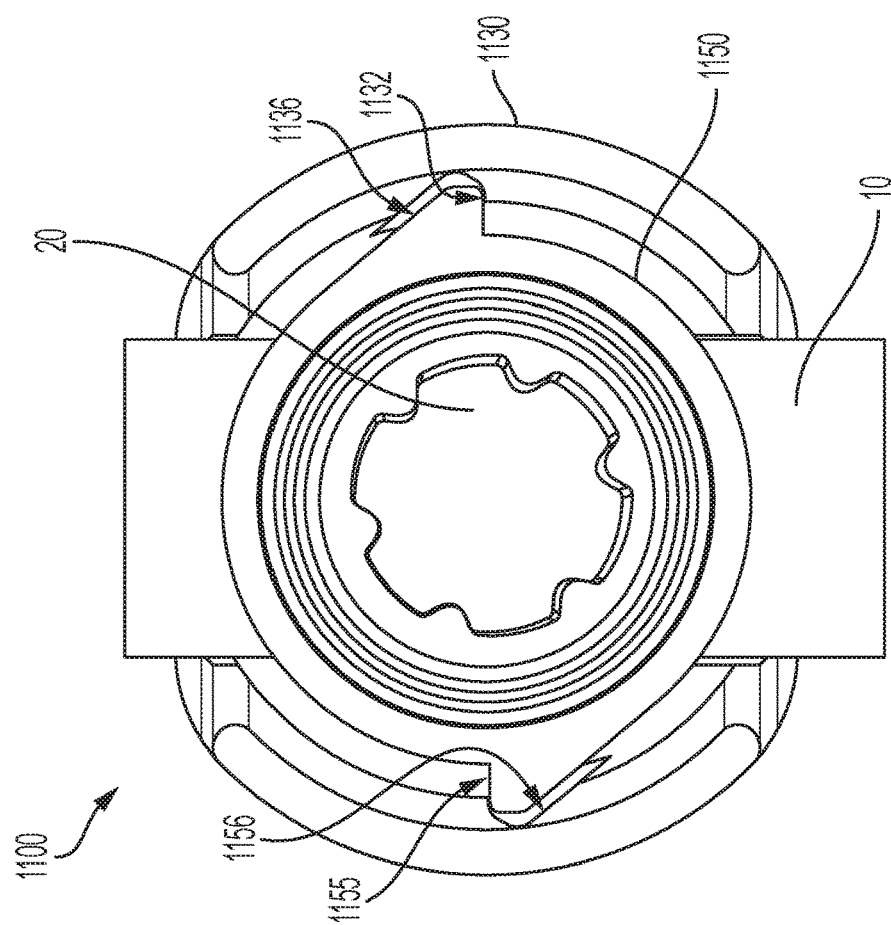
FIG. 13 is a top view of the arrangement of FIG. 12.

110. An example setscrew 20 is shown in FIGS. 12-14, illustrating a related but distinct embodiment of the present technology. In each embodiment, as with the rod 10, the setscrew 20, can be part of the system 100, or simply used with it. Any of the components described—cap, receiver, rod, setscrew, bonescrew (not shown), cap-removing tool or instrument (not shown), etc.—can be made, sold, distributed, stored, or otherwise provided together, such as in a surgical kit or set.

In various embodiments, each receiver arm 130 has a proximal flange or protrusion 132 and a distal protrusion or shelf 133 extending radially inward from a primary wall 131. The protrusions 132, 133 define a cap-receiving compartment or cavity 136 between them.

The proximal protrusion 132 has opposing sloped receiver pop-on surfaces 134. In various embodiments, each receiver pop-on surface 134 is a proximal surface of the protrusion 132 extending radially inward and distally. Each receiver pop-on surface 134 may in any portion of it be rounded, curved, beveled, or otherwise not perfectly straight, including at one or both of a distal edge and a proximal edge of the surface 134 and intermediate the edges.

The cap 150 has opposing cap pop-on/splay-resisting wings or flanges 160. The flanges 160 each extend along a common radial line of the cap 150 from a primary wall 161 of the cap 150. Each flange 160 is in various embodiments positioned at a distal end of the cap 150.

Each flange 160 has a pop-on surface 162, which in various embodiments is at a radially extreme and distally extreme portion of the flange 160.

With further reference to FIG. 2, each cap pop-on surface 162 is angled or sloped in various embodiments. The cap pop-on surfaces 162 may be rounded, curved, beveled, or otherwise not perfectly straight, at any point, including at one or both edges (distal and proximal edges) and intermediate the edges.

The cap 150 and receiver 110 are sized and shaped such that when the cap 150 is axially 30 centered over, and moved distally into contact with, the receiver 110, with cap anti-rotation flanges or wings 170 aligned over inter-arm gaps, the cap pop-on surfaces 162 contact the corresponding receiver pop-on surfaces 134.

The flanges 160 and wings 170 are in various embodiments generally co-planer. Benefits of having them on the same plane, or close to each other planarly, include the ability to keep the height down. A smaller profile cap requires less material, is lighter, and can have these qualities without compromising strength for the described functionalities.

The receiver and cap pop-on surfaces 134, 162 are angled or sloped such that after the cap 150 contacts the receiver 110 at the surfaces 134, 162, and the cap is forced further distally, each cap pop-on surface 162 slides distally along the corresponding receiver pop-on surface 134. The radially outward-facing cap pop-on surfaces 162 pushing on the inward-facing receiver pop-on surfaces 134 forces the arms 130 to move slightly away from each other, or splay. This allows the cap flanges 160 to clear proximal receiver protrusions 132, to lock into the receiver 110, as the cap is moved further distally.

As indicted in FIG. 2, each receiver pop-on surface 134 extends at an angle 115, and each corresponding cap pop-on surface 162 extends at an angle 163, with respect to a horizontal reference frame.

Each cap pop-on surface 162 extends in various embodiments at the angle 163 being between about 45 degrees and about 85 degrees. In some cases, the range is smaller, such as between about 50 degrees and about 80 degrees. These are only examples, and the cap 150 can be designed so that the angle 163 has any value or range within these ranges, or beyond these ranges. The angle 163 is in various embodiments at least between 0 degrees and 90 degrees.

In a contemplated embodiment, the cap pop-on surface 162 is a distal, proximally extreme corner of the cap.

For embodiments in which the cap 150 has an angled, sloped, rounded, or beveled, pop-on surface 162, benefits of the cap pop-on surface 162 having these angles, or related rounding or beveling, with sufficiently corresponding angulation of the receiver pop-on surface 134, include the surface 162 being able to cause the receiver arms 130 to splay when the surface 162 is pushed distally against the receiver pop-on surface 134 with sufficient force, to push the receiver pop-on surface 134, and so the receiver arms 130 by an amount sufficient to allow the cap flange 160 to pass distally beyond the receiver proximal protrusion 132.

Each receiver pop-on surface 134 extends in various embodiments at the angle 115 being between about 45 degrees and about 85 degrees. In some cases, the range is smaller, such as between about 50 degrees and about 80 degrees. These are only examples, and the receiver 110 can be designed so that the angle 115 has any value or range within these ranges, or beyond these ranges. The angle 115 is between 0 degrees and 90 degrees.

Benefits of the receiver pop-on surface 134 having such angle 115 include the surface 134 being configured to cause the receiver arms 130 to splay, when the cap pop-on surface 162 is pushed distally against the receiver pop-on surface 134, by an amount sufficient to allow the cap flange 160 to pass distally beyond the receiver proximal protrusion 132. The angle 115 is selected to facilitate the maneuver in response to a pre-determined distal force on the cap 150 below an undesirable force. The system 100 is designed so that it is not too difficult for a user to pop the cap 150 into the receiver 110.

System characteristics facilitating the pop-on maneuver can also include thickness and material of portions or all of the receiver arms 130, and in some cases size, shape, and material of the receiver base 120, such as proximal portions of the base 120. The receiver 110 can also be sized, shaped, and have material allowing the arms to spring back, toward their original position, after the cap flanges 160 have passed distally beyond the proximal receiver protrusion 132.

In various embodiments the cap 150 and receiver 110 are configured such that angles 165, 115 of the respective pop-on surfaces 162, 134 are generally the same, or within a predetermined angle, or percentage of angulation, from each other. The surfaces can be configured such that the correspondence provides robust, or maximizes, surface-to-surface contact, so that force applied to the receiver pop-on surface 132 by the cap pop-on surface 162 is distributed, as opposed to being more of a point force.

FIG. 2 also shows that each flange 160 also has a proximally facing cap lock, or splay-resisting, surface 164. The receiver 110 has a corresponding, distally facing, receiver lock, or splay-resisting, surface 138. Function of these surfaces is described further below, including in connection with FIG. 7.

Figure 3:
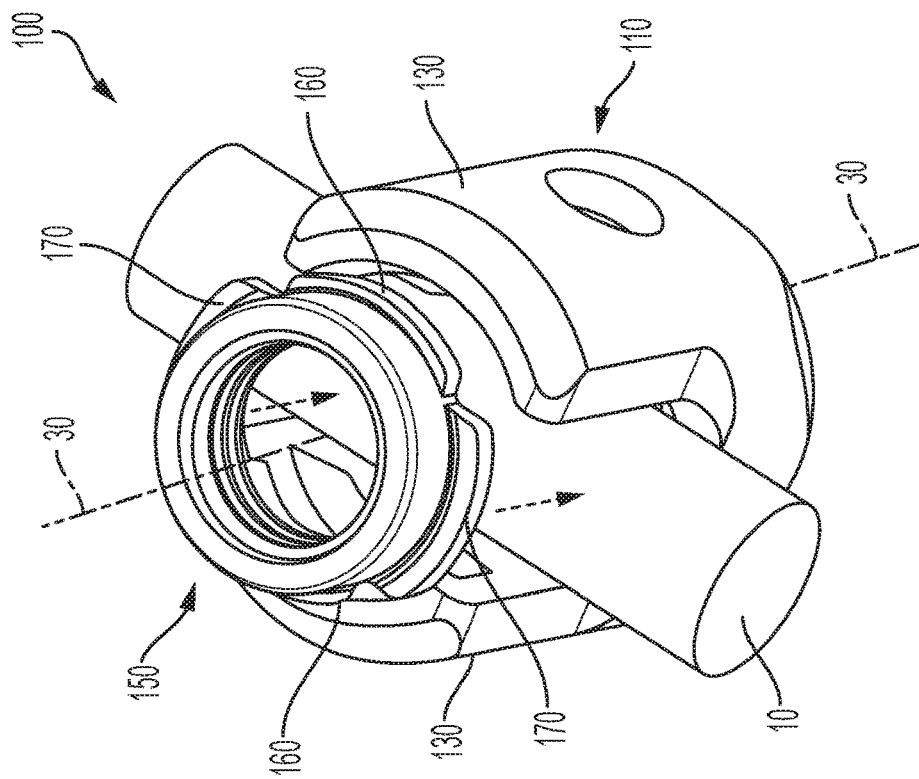
FIG. 3 is a is a perspective view of the maneuver of FIG. 2.

FIG. 3 is a is a perspective view of the maneuver of FIG. 2, showing the cap 150 being lowered onto the receiver 110 along the receiver longitudinal axis 30. This view shows the cap anti-rotation flanges or wings 170 extending radially outward generally perpendicular to a direction that the cap pop-on flanges 160 extend radially outward. The cap wings 170 are as mentioned aligned over inter-arm 130 gaps for the pop-on maneuver.

Figure 4:
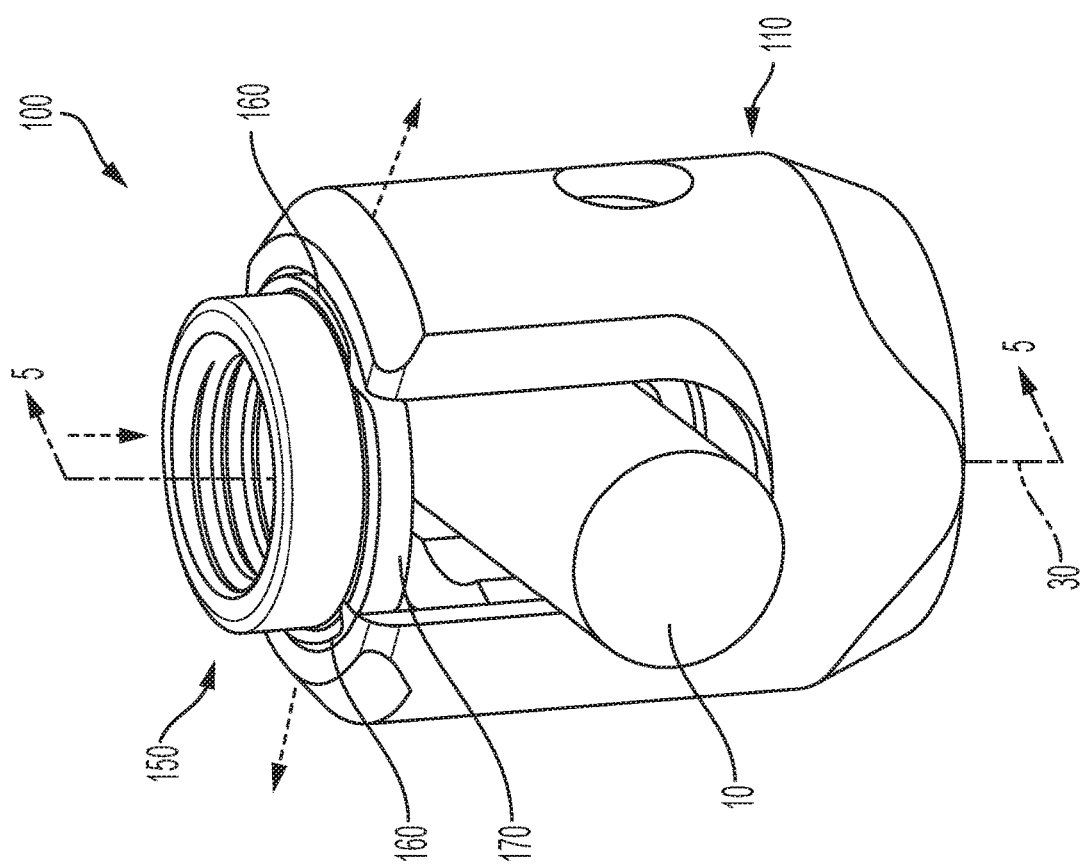

FIG. 4 is a perspective view showing the pop-on cap 150 moved further distally to contact the receiver 110. As shown, as the cap 150 is moved into contact with the receiver 110, the opposing anti-rotation wings 170 of the pop-on cap 150 become disposed between adjacent arms 130 of the receiver 110.

As the cap 150 is pushed further distally with respect to the receiver 110, forces from the cap pop-on surfaces 162 of cap flanges 160 against the receiver pop-on surfaces 134, push the receiver pop-on surfaces 134, and so the receiver arms 130, splay, moved radially away from each other, or laterally away from the longitudinal axis 30.

Figure 5:
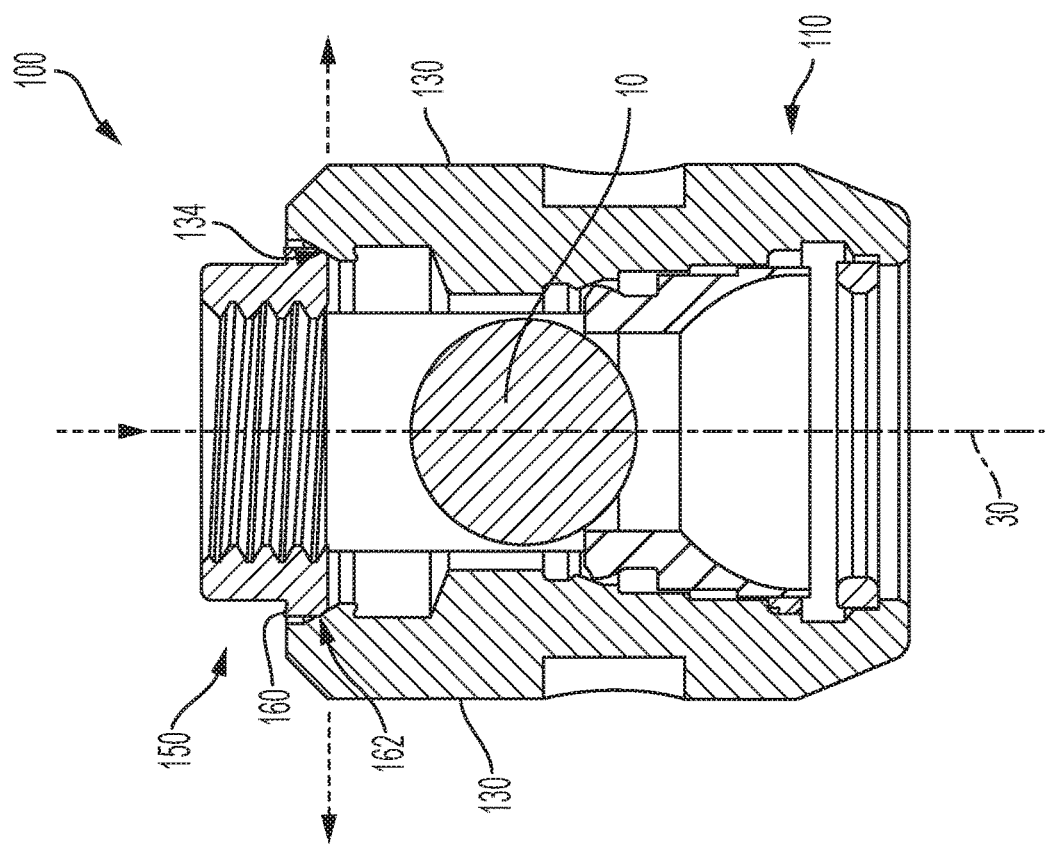
FIG. 5 is a side cross section taken along line 5-5 of FIG. 4.

FIG. 5 is a side cross section taken along line 5-5 of FIG. 4. Starting of the forced arm 130 splaying, as the cap pop-on surfaces 162 are pushed against the receiver pop-on surfaces 134, is indicated schematically in FIGS. 4 and 5 by opposing radial arrows.

Figure 6:
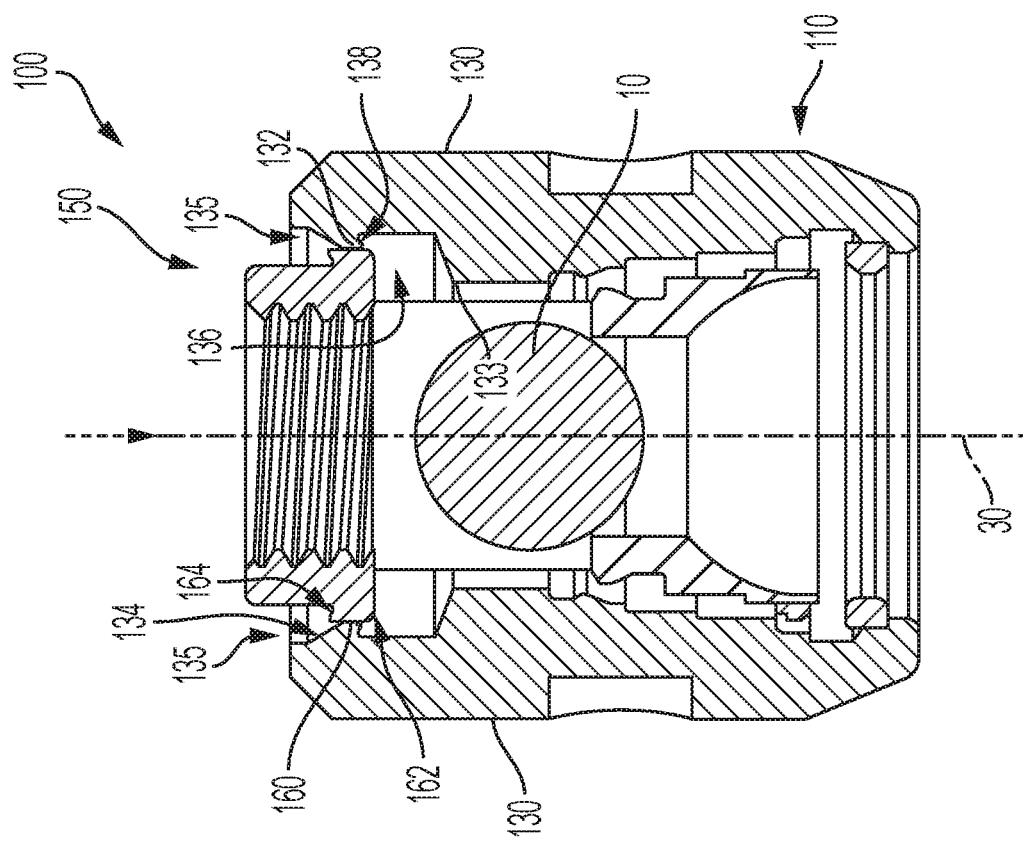
FIG. 6 is a side cross section showing the cap being popped on, the cap forcing receiver arms to splay slightly to allow the cap to move distally to a locking position in the receiver.

FIG. 6 is a side cross section showing the pop-on cap 150 having been pushed further distally with respect to the receiver 110. The opposing receiver arms 130 are shown slightly splayed, having been pushed apart by the radially outward forces effected at the receiver pop-on surfaces 134 by the distal pushing from the cap pop-on surfaces 164.

Figure 7:
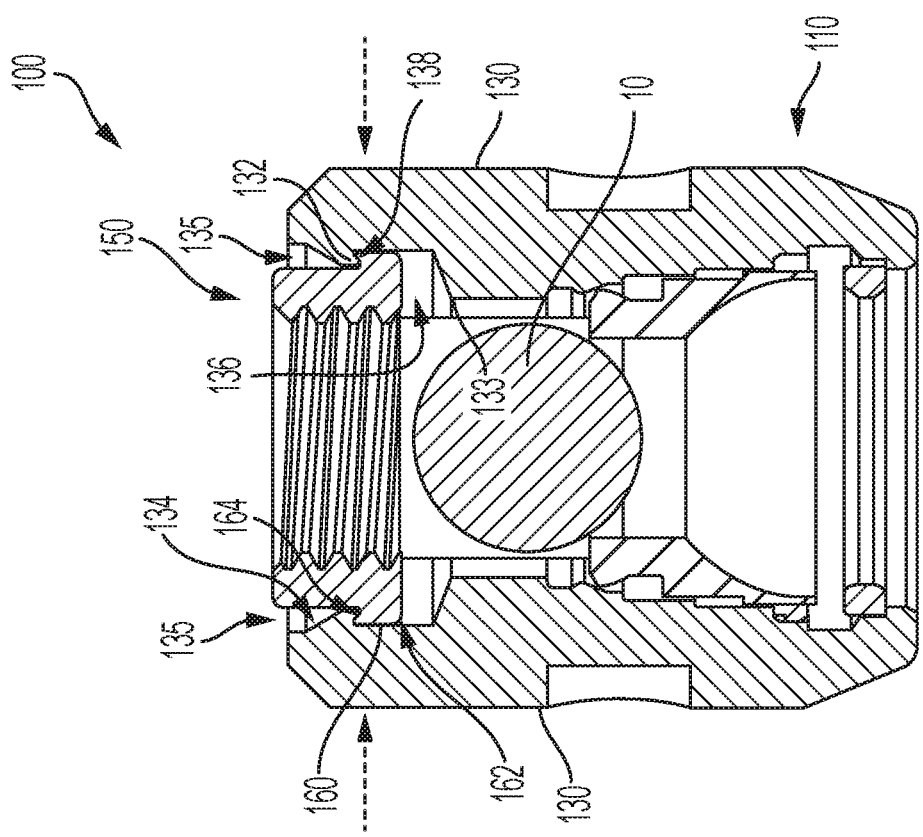
FIG. 7 is a side cross section taken along line 7-7 of FIG. 8, showing the cap popped onto the receiver.
Figure 8:
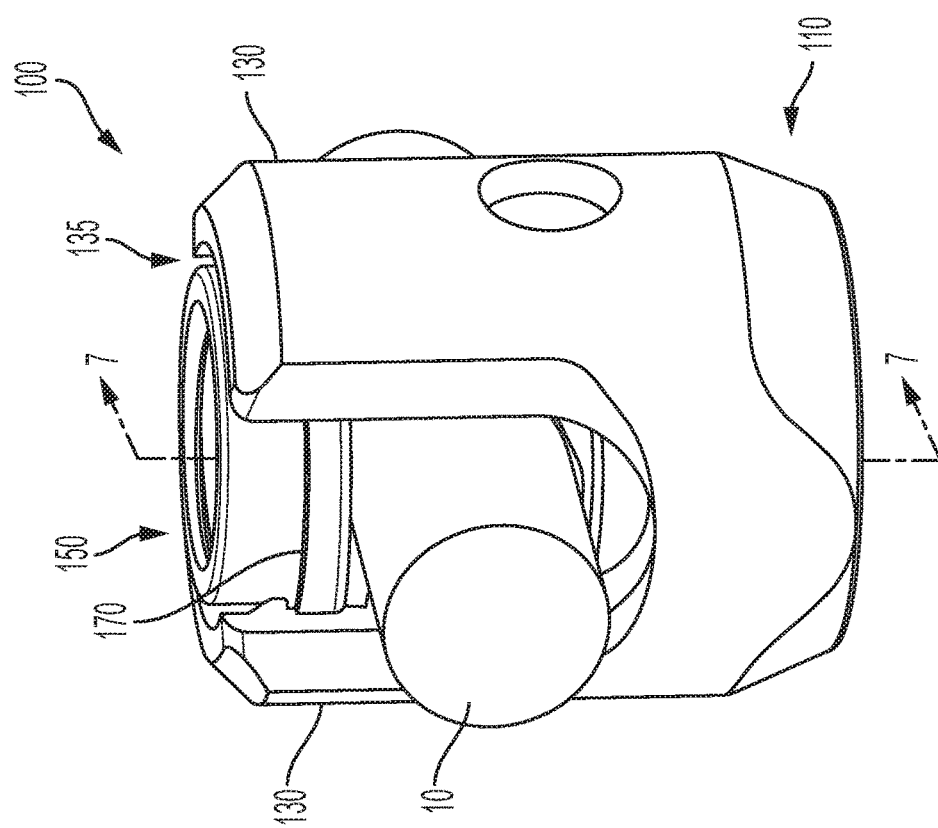
FIG. 8 is a side view of the state shown in FIG. 7.

FIG. 7 is a side cross section, taken along line 7-7 of FIG. 8, showing the pop-on cap 150 after it has been forced further distally with respect to the receiver 110, from the state of FIG. 6. After the pop-on cap flange 160 moves distally past the proximal receiver protrusion 132, the mentioned cap-to-receiver pop-on force ceases, and so the receiver arms 130 spring back toward their original position. That is, the forced splay is relieved. The receiver arms 130 moving back, radially inward, is indicated by opposing arrowed lines in FIG. 7.

After the pop-on cap flange 160 clears the proximal receiver protrusion 132, and the receiver arms 130 are thereby allowed to move back in, no longer being held apart by the cap flanges 160, the cap flanges 160 become disposed within the cap-receiving cavity 136 of the receiver 110.

The maneuver also positions each of the opposing proximally facing cap splay-resisting surfaces 164 adjacent and facing a corresponding receiver splay-resisting surface 138. The two surfaces are configured (sized, shaped, positioned, oriented, etc.) to engage, or interlock. The interlock prevents the receiver arms 117 from moving away from each other, or splaying, undesirably after the engagement. In some embodiments, the cap 150 and receiver 110 are configured such that the surfaces 164, 138 end up generally flush against each other, or at least flush along one or more portions of the surfaces 164, 138.

Each receiver splay-resisting surface 138 extends in various embodiments at an angle 117 with respect to the horizontal reference frame of between about 5 degrees and about 75 degrees. In some cases, the range is smaller, such as between about 10 degrees and about 45 degrees. These are only examples, and the receiver 110 can be designed so that the angle 117 has any value or range within these ranges, or beyond these ranges. The angle 117 is at least between 0 degrees and 90 degrees.

Benefits of the receiver splay-resisting surface 138 having these angles, with sufficiently corresponding angulation of the cap splay-resisting surface 164, include the surface 138 being angled aggressively enough to create a robust connection with the splay-resisting surface 164 of the cap 150 for resisting receiver arm splay, or, partially locking the arms 130 against unwanted arm splay, such as in tightening of the set screw in the receiver 110 and onto the rod 10, but slight enough such that removal of the cap 150 by splaying the receiver arms 130 intentionally, in a potential revision procedure, after the initial surgery implanting the system 100 (e.g., years later), is relatively easy with sufficient force separating the arms 130.

Variables for facilitating the robust connection and/or the relatively easy release can also include length and width of the surfaces 164, 138, and material of the surfaces 164, 138, of the cap flange 160 and receiver protrusion 132.

Each cap splay-resisting surface 164 extends in various embodiments at an angle 165 with respect to the horizontal reference frame of between about 5 degrees and about 75 degrees. In some cases, the range is smaller, such as between about 10 degrees and about 45 degrees. These are only examples, and the cap 150 can be designed so that the angle 165 has any value or range within these ranges, or beyond these ranges. The angle 165 is at least between 0 degrees and 90 degree.

Benefits of the cap splay-resisting surface 164 having these angles, with sufficiently corresponding angulation of the receiver splay-resisting surface 138, include, again, the surface 164 being angled aggressively enough to create a robust connection with the splay-resisting surface 138 of the receiver 110, to lock the receiver arms 130 against unwanted splay, such as in tightening of the set screw in the receiver 110 and onto the rod 10, but slight enough for removal of the cap 150 by intentional splaying of the receiver arms 130 to be relatively easy with sufficient force separating the arms 130.

In various embodiments, the cap 150 and receiver 110 are configured such that angles 165, 117 of the respective splay-resisting surfaces 164, 138 are generally the same, or within a predetermined angle or percentage of angulation from each other. An entirety, or portions of the surfaces in some embodiments end up flush against each other when the system 100 is in the locked position shown in FIGS. 7-9.

While the splay-resisting surfaces 138, 164 are shown contacting in FIG. 7, in various embodiment, this contact is not automatically fostered simply by the cap flange 160 clearing the proximal receiver protrusion 132 and entering the cap-receiving cavity 136. The receiver arms 130, including the cap-receiving cavities 136 defined partially thereby, are as mentioned sized and shaped to allow the cap flanges 160 to, upon clearing the proximal receiver protrusions 132, become disposed in the cavities 136. For embodiments in which the receiver 110 includes the distal protrusion 133, the distal protrusions 133 of the receiver 110 must be sufficiently spaced from the proximal protrusion 132 to allow clearance for the disposals. In a contemplated embodiment, the receiver 110 does not include the distal protrusion or shelf 133, or it is less pronounced.

In assembling of the system 100, after the cap flanges 160 of the cap 130 clear the proximal receiver protrusion 132, the cap can be moved proximally by threading the setscrew within the cap 150. This is done using a setscrew driver (not shown). An example setscrew 20 is shown in FIG. 12, in connection with another embodiment of the present technology. The setscrew is threaded distally through the pop-on cap 150 threadform 152 until a distal tip of the setscrew contacts the rod 10 positioned between the arms 130 of the receiver 110. At this point, relative position between the setscrew and the rod is generally fixed. As the setscrew is threaded further through the cap 150, the cap is moved proximally by the continued threading action, as the setscrew generally does not move any further distally with respect to the rod 10.

The pop-on cap 150 is moved proximally in this way until the cap flanges 160 contact the proximal receiver protrusion 132 robustly. The respective splay-resisting surfaces 138, 164 thereby engage and are kept in contact. A component of forces that the proximally facing splay-resisting surface 164 of the cap 150 exerts on the distally facing splay-resisting surface 138 of the receiver 110 is radially inward, preventing the receiver lock surfaces 138 from moving away from each other, and thereby preventing splay of the arms 130.

FIG. 8 is a side view of the system state shown in the cross-section FIG. 7. The view shows the anti-rotation wings 170 of the pop-on cap 150 disposed between respective arms 130 of the receiver 110. The wings 170 keep the pop-on cap 150 from rotating in either direction, such as when a user is tightening/loosening a setscrew into/out of the cap 150.

Figure 9:
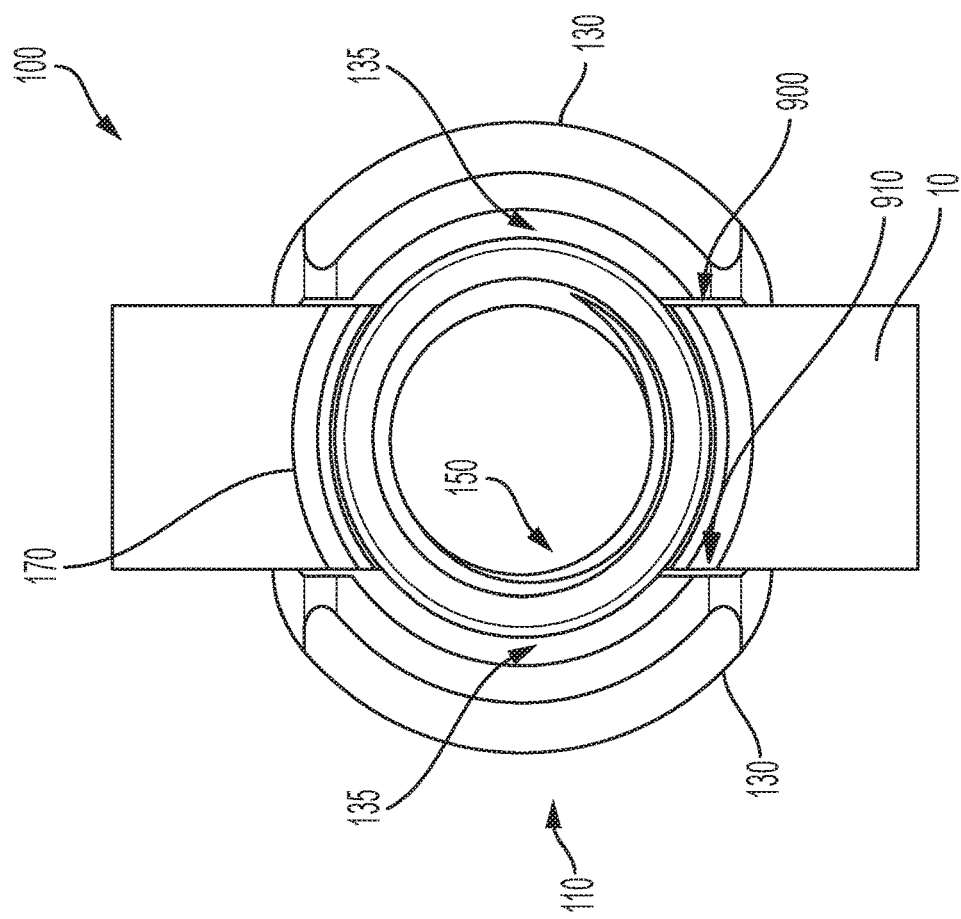
FIG. 9 is a top, plan, view of the state of the same.

More particularly, with reference to plan view of FIG. 9, when the setscrew is turned in the installed cap 150, the cap 150 is kept from rotating by edges 900 (four of them, e.g.) of the two anti-rotation wings 170 contacting adjacent edges 910 (four of them, e.g.) of the receiver arms 130.

A user may need to remove the pop-on cap 150, after the initial surgery implanting the system 100 (e.g., years later), in a revision procedure, in which the rod 10 needs to be removed or adjusted. A cap-removing instrument or tool (not shown) can be used. In various embodiment, the instrument has a distal end or ends sized and shaped to fit within a gap 135, defined between the proximal end of the receiver 110 and the proximal end of the cap 150, and effect intentional receiver splay by forcing the arms 130 laterally outward while positioned in the gap 135. The gap 135 is called out in FIGS. 7-9. Alternately, an instrument can apply lateral forces by applying a force to the interior walls of the receiver arms 130.

The proximal end of the receiver 110 include a proximal inner surface, adjacent and in some cases defining the gap 135. The surface facilitates the revision splaying. The proximal inner surface can be slanted, for instance, so that the splaying instrument when pushed distally against the surface slides along the proximal inner surface thereby forcing the proximal inner surfaces, and so the arms 130, radially outward. In a contemplated embodiment, the proximal inner surface of the receiver arms 130 has a notch, slot, or other element that the instrument can secure or connect to in order to facilitate robust contact between the instrument and surface, and forcing of the proximal inner receiver surface radially outward. In another contemplated embodiment, the inner surface is not slanted, or only slanted only slightly, and the instrument upon being placed in the gap 135 forces the arms 130 apart by applying force radially outward on the walls, without any, or without much, relative siding between the instrument and the proximal inner receiver surface.

As the arms 130 splay, the splay-resisting interfaces 136, 164 are pushed apart, namely the receiver splay-resisting surfaces 136 are forced to move radially outward, along and then off of the cap splay-resisting surfaces 164. The cap 150 is then free from the receiver 110, and can be removed in the proximal direction from the receiver 110. In various embodiments, the instrument has a capture design for grasping, engaging, or otherwise persuading the cap 150 to move proximally, out of the receiver 110, while the arms 130 are splayed by the instrument. Or a separate cap removing instrument, such as one that can fit within, around, or aside of the splaying instrument, can persuade the cap 150 proximally out of the receiver 110. Such removing feature or instrument can have an external thread, for instance, for engaging with the internal thread of the cap 150.

Figure 10:
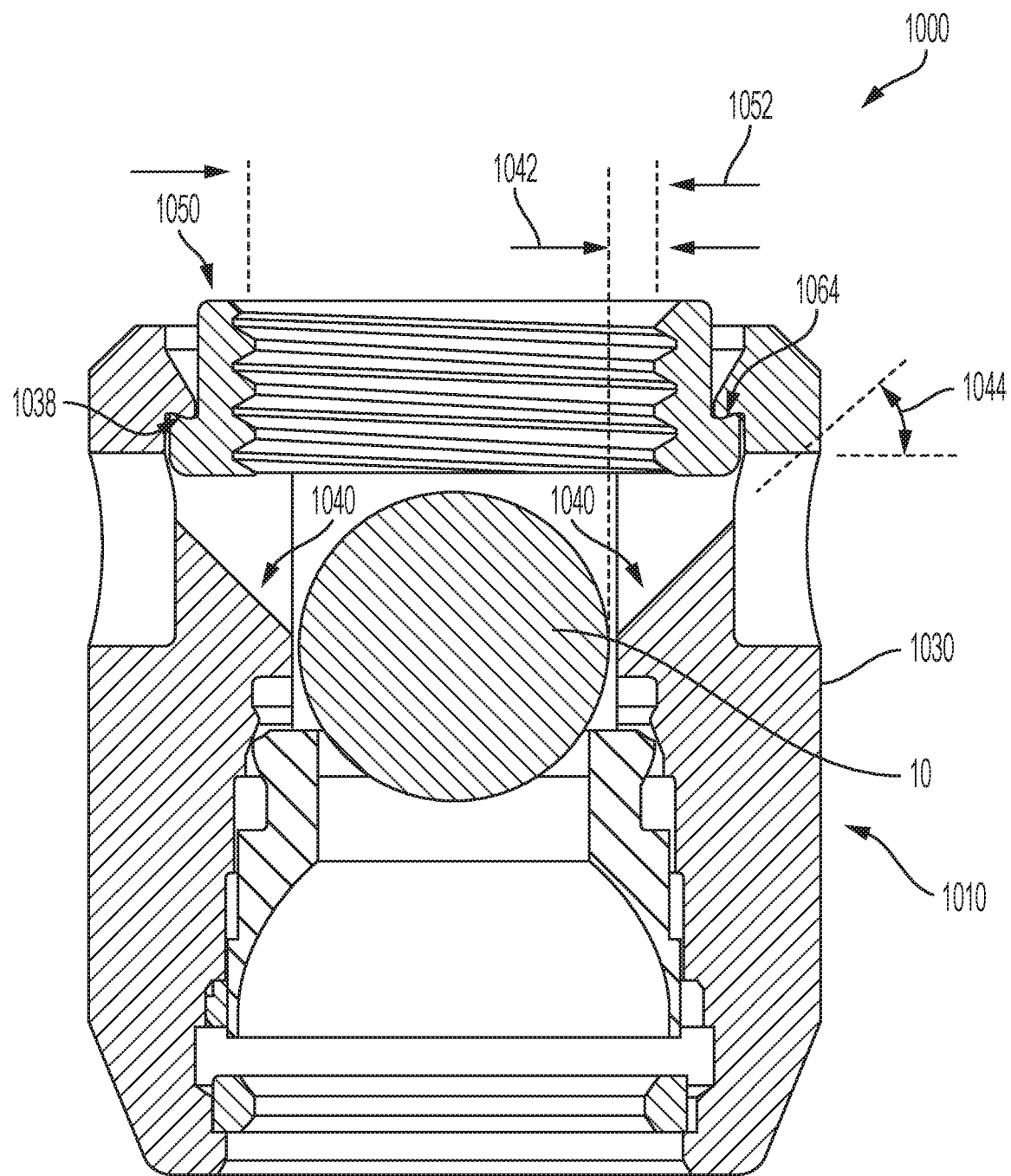
FIG. 10 is a side cross section of a cap and receiver according to a second embodiment of the present technology.

With continued reference to the three main embodiments of the present disclosure, FIG. 10 shows a system 1000 according to the second main embodiment. FIG. 10 shows a side cross section of an alternative pop-on cap 1050 and receiver 1010, according to this embodiment.

The pop-on cap 1050 and receiver 1010 of this embodiment is in many ways like the cap and receiver 150, 110 of the first main embodiment, of FIGS. 1-9. One primary distinction is that the pop-on cap 1050 of this embodiment is designed to have a larger inner diameter (ID) 1052 (and in most cases also, then, a larger outer diameter (OD)) than that of the cap 150 of the first embodiment. The cap 150 of the first embodiment is in some cases sized to receive a standard setscrew. The cap 1050 of FIG. 10 is in various embodiments sized to receive a unique setscrew, having a larger-than-standard outer diameter, or thread diameter.

As another important distinction, due to the larger cap 1050 in this embodiment, the receiver 1010 is also larger to accommodate the cap 1050. For example, the arms 1030 are spaced apart farther from each other for the system 1000 of this embodiment as compared to separation between the arms 130 of the receiver 110 of the system 100 of the first embodiment.

Another primary distinction between the system 1000 of FIG. 10 and the system 100 of FIGS. 1-9 is that the receiver 1010 of this embodiment has a pronounced inward-and-downward-slanting or -sloped wall 1040. The wall 1040 extends radially inward farther than the ID 152 of the pop-on cap 1050, as shown in FIG. 10. That is, each of the walls 1040 extend distally and radially into a cylindrical plane defined by the ID of the cap 1050.

In various embodiments, the cap ID 1052 is between about 7.0 mm and about 8.0 mm. In various embodiments, each slanted wall 1040 extends radially inward to within the cylindrical plane of the cap OD 1052 by a protruding distance 1042 of between about 5.0 and about 6.0 mm.

The slanted wall 1040 extends at an angle 1044 with respect to a horizontal reference frame. In various embodiments, the wall 1040 is oriented at an angle 1044 of between about 30 degrees and about 60 degrees. In some cases, the range is smaller, such as between about 35 degrees and about 55 degree, or between 40 and 50 degrees. These are only examples, and the cap 150 can be designed so that the angle 163 has any value, such as about 45 degrees, or range within said ranges, or beyond these ranges. The angle 1044 is between 0 degrees and 90 degrees.

For removing the cap 1050 of this embodiment, such as in a revision procedure, the cap ID 1052 is sized, and the slanted wall 1040 sized, oriented, and positioned, to permit a splaying instrument or tool (not shown) to extend distally through the central cavity of the cap 1050 and into contact with the slanted wall 1040.

For revision procedures, a surgeon can remove the internal setscrew 20 and then load the splaying instrument through the cap to contact the internal tapered portion 1040 such as to splay the walls open for removal of cap 1050.

For cases in which the instrument is used while the rod 10 is still positioned in the receiver 110, the instrument may have a hollow sized to receive the rod 10. In this way, the rod 10 does not interfere with the function of contacting and pressing sufficiently against the slanted surface 1040 by the splaying instrument. Or the splaying instrument may have two or more arms or prongs extending distally from a body of the tool such that the rod 10 does not interfere with the instrument contacting and pushing against the receiver splay surfaces 1040.

After the distal tips of the splaying instrument contact the receiver splay surfaces 1040, the instrument is pushed further distally, applying more force to the surfaces 1040. The tips in this slide along the surfaces 1040 as radially outward components of the force applied by the tips onto the surfaces 1040 cause the surfaces 1040, and so the receiver arms 1030 to move away from each other, or splay.

As the arms 1030 splay, the splay-resisting interfaces 1036, 1064 are pushed apart, the cap locking surfaces 1064, and so the cap flanges on which the locking surfaces are on, become free from the receiver arm locking surfaces 1038, and so free of the receiver proximal protrusions on which the arm locking surfaces are on. The freedom allows the cap 1050 to be removed in the proximal direction from the receiver 1050. In various embodiments, the instrument has a capture design for grasping, engaging, or otherwise persuading the cap 1050 to move proximally, out of the receiver 1010, while the arms 1030 are being splayed by the instrument. Or a separate cap removing instrument or tool, such as one that can fit within, around, or aside of the splaying instrument, can be used.

Any other features of the system 1010 of this embodiment can be similar or identical to corresponding features of the system 100 described in connection with FIGS. 1-9.

Figure 11:
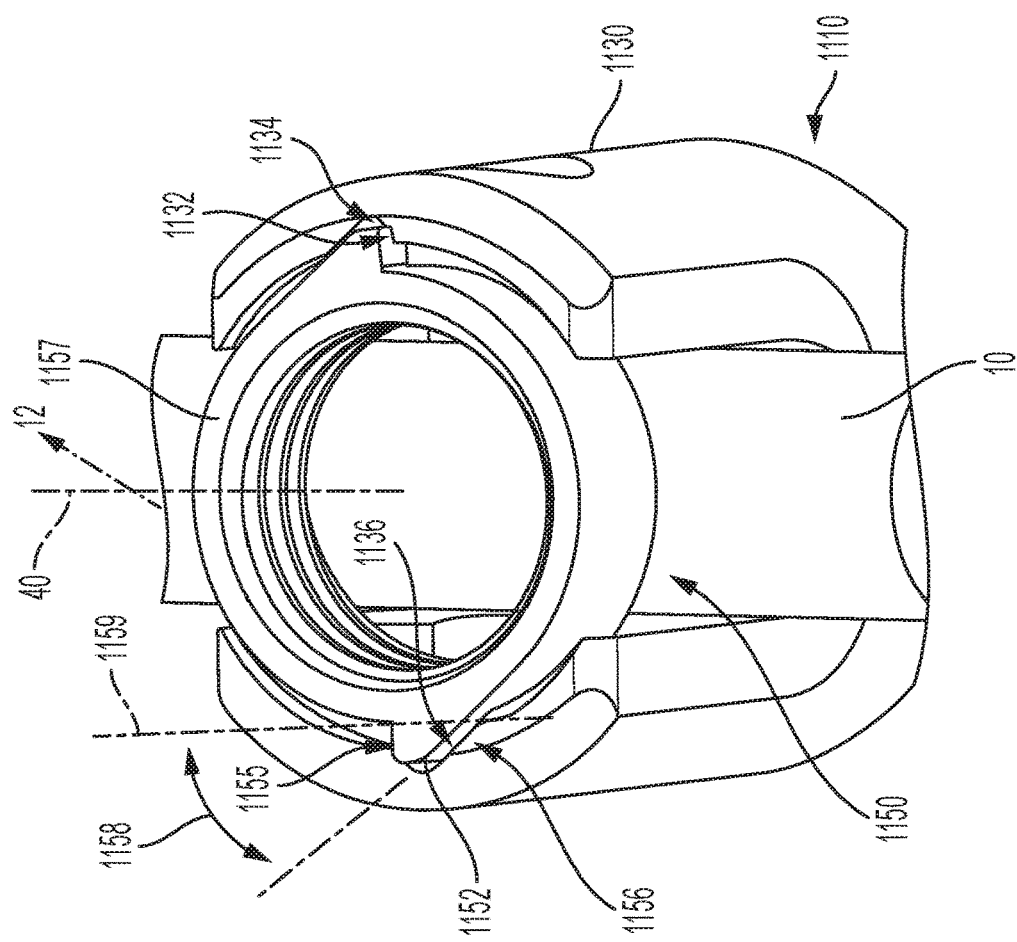
FIG. 11 is a perspective view of a cap and receiver according to a third embodiment of the present technology.

Turning to the third main related embodiment, FIGS. 11-14 show a system 1100 again having a pop-on cap 1150 and receiver 1110. FIG. 11 is perspective view showing the system 1100 after the cap 1150 has been popped onto the receiver 1110.

For initially securing the cap 1150 to the receiver 1110, the cap 1150 is lowered toward the receiver 1110 along a system axis 40. The cap 1150 is orientated for the maneuver with opposing rotation-preventing/rotation-resisting wings 1152 aligned, or positioned, over wing-receiving cavities 1134 of the receiver 1110. The cap 1150 is popped onto the receiver 1110 in a manner similar to the pop-on maneuver described above in connection with the embodiments of FIGS. 2-7. The cap 1150 and receiver 1110 are further configured (e.g., sized and shaped) such that splaying of the receiver arms 1130 is resisted, in a manner similar to how splaying of the receiver 110 is resisted after cap 150 installation was described in connection with the embodiments of FIGS. 1-9 and 10.

FIG. 12 shows receiver and cap splay-resisting-resisting, or locking, surfaces 1138, 1164, like those of the embodiments of FIGS. 1-9 and 10. These engage upon popping on the cap 1150, and in some cases only after also threading the setscrew sufficiently into the cap 1150, as described above regarding other embodiments.

The cap rotation-resisting/splay-promoting wings or protrusions 1152 are configured to prevent the cap 1050 from rotation in one direction, and to resist the cap from rotating in another direction, after the cap 1150 has been popped onto the receiver 1110 and when torque is applied to the cap 1050. Namely, for instance, the wings 1152 are configured (e.g., sized and shaped) to prevent the cap 1150 from rotating in a first direction with respect to the receiver 1110—clockwise in the example of FIG. 11. And the wings 1152 are configured in various embodiments to resist rotating of the cap 1150 in the opposite direction—counterclockwise in the example of FIG. 12).

Proximal ends of receiver arms 1130 have shapes corresponding to shaping of the wings 1152 to effect the prevention and resistance functions. The proximal end of each arm 1130 includes the wing-receiving cavity 1134 sized and shaped to receive the cap wing 1152.

For the rotation-preventing function, rotation of the cap 1150 with respect to the receiver 1110 is prevented by a cap rotation-preventing surface 1155 of the wing 1152 contacting a corresponding receiver rotation-preventing surface 1132 of the proximal end of the receiver 1110. In various embodiments, the cap rotation-preventing surface 1155 extends radially from a cylindrical body 1157 of the cap 1150. The prevention is promoted further by splay-resisting functionality, like that of the first wo main embodiments, keeping the arms 1130 from splaying.

Each of the receiver and cap anti-rotation surfaces 1132, 1155 may extend generally orthogonal to a tangent 1159 of the cylindrical body 1157. In other embodiments, either or both are angled by more or less than 90 degrees with respect to the tangent, such as within a range of about 75 degrees to about 90 degrees.

Further regarding the resisting functionality, while the cap wings 1152 and cavity 1134 are configured such that rotation in the first direction (e.g., clockwise) is prevented altogether, rotation in the second direction (counterclockwise) is only resisted. That is, rotation of the cap in the receiver is hindered, but possible in response to sufficient torque placed on the cap in the second direction.

The receiver rotation-preventing surface 1132 can extend at generally the same or similar angle as the cap rotation-preventing surface 1155. The surfaces 1155, 1132 can be generally, or close to, flush with each other, for instance, when the cap 1150 is popped onto the receiver 1110.

The opposing rotation-preventing/rotation-resisting wings 1152 in various embodiments have shape that may be referred to as a teardrop, as shown in FIG. 11, or similar descriptive terms, as the wing profile can be generally demi- or half-teardrop shaped, such as shown in the figures. The shape in various embodiments includes a first, cap rotation-resisting, surface 1156 extending at a slighter angle 1158 from the body 1157 of the cap 1150, as compared to an angle (e.g., 90 degrees) at which a second, cap rotation-preventing, surface 1155 extends from the cap body 1157. A receiver rotation-resisting surface 1136 may be angled to the same or similar corresponding disposition, promoting robust contact between the surfaces 1156, 1136, at least when torque in the second direction (e.g., counterclockwise) is applied to the installed cap 1150.

The cap rotation-resisting surface 1156 may extend, for instance, at an angle 1158 of between about 10 degrees and about 45 degrees, with respect to the cap body tangent 1159. The angle 1158, which may be greater or smaller than this range, is configured (e.g., sized, shaped, and oriented) such that the receiver rotation-resisting surface 1156 interfaces with a corresponding wall 1136 of the receiver gap 1134 when torque is applied in the second direction (e.g., counterclockwise locking down, distally, in FIG. 12) to the cap 1150. As the torque is applied, the surface-to-surface 1156, 1136 interfacing resists rotating of the cap 1150 in the second direction with respect to the receiver 1110, but does not resist rotation of the cap 1150 in the second direction with respect to the receiver 1110 completely.

Torque can be applied to the cap 1150 in any of a variety of ways to force intentional splay of the arms 1130. The system 1100 can include or be used with an instrument or tool (not shown) configured at its distal end to engage a proximal portion of the wings 1152, for instance, and apply at least said pre-determined amount of torque to the cap 1150 in the second direction (e.g., counterclockwise), the force being sufficient to overcome friction between the rotation-resisting surfaces 1156, 1136. The cap surface 1156 can thereby slide with respect to the receiver surface 1136, as described, enabling the cap 1150 to rotate with respect to receiver 1110, thereby splaying the arms 1130 for cap removal. As can be seen in FIGS. 11 and 14, the proximal surface of the wings 1152 can extend higher (farther proximally) than an adjacent proximal surface of the receiver arms 1130. The exposed proximal portion of the cap wings 1152 provides real estate that the instrument can interface with to apply torque to the cap 1150 in the second direction. The instrument can apply torque against the portion of the anti-rotation surfaces 1155 of the wings 1152 extending above the arms 1130, for instance.

The surfaces 1156, 1136 are configured such that, upon application of at least a predetermined amount of torque to the cap 1150 in the second direction, the cap 1150 rotates in the second direction with respect to the receiver 1110, with the rotation-resisting surface 1156 of the cap 1150 sliding along the rotation-resisting surface 1136 of the receiver 1110.

A component of forces that the cap rotation-resisting surfaces 1156 apply to the receiver rotation-resisting surfaces 1136, sliding in the second direction (e.g., counter-clockwise) along the receiver rotation-resisting surfaces 1136, is a radial force. As the radial force is applied to the receiver rotation-resisting surfaces 1136, and thereby to the receiver arms 1130, the arms 1130 are intentionally splayed.

As the receiver arms 1130 of this embodiment are splayed intentionally, the splay-resisting interfaces 1138, 1164 are pushed apart, namely the receiver splay-resisting surfaces 1138 are forced to move radially outward, along and then off of the cap splay-resisting surface 1164. The cap 1150 is then free from the receiver 1110, and can be removed in the proximal direction from the receiver 1110. In various embodiments, the splaying instrument has a capture design for grasping, engaging, or otherwise persuading the cap 1150 to move proximally, out of the receiver 1110, while the arms 1130 are splayed by the instrument. Or a separate cap removing instrument, such as one that can fit within, around, or aside of the splaying instrument, can persuade the cap 1150 proximally out of the receiver 1110 while the arms 1130 are splayed. Such removing feature or instrument can have an external thread, for instance, for engaging with the internal thread of the cap 1150.

FIG. 12 is a cross section taken along line 12 of FIG. 11. The view shows the system 1110 after the setscrew 20 has been threaded into the cap 1150, locking down the rod 10 in the receiver 1110, and locking the cap locking surfaces 1164 against the receiver locking surfaces 1138, thereby preventing unwanted receiver splay.

FIG. 13 is a top, plan, view of the arrangement of FIG. 12, with the setscrew 20 intact. And FIG. 14 is a perspective view of the arrangement of FIGS. 12 and 13.

Figure 15:
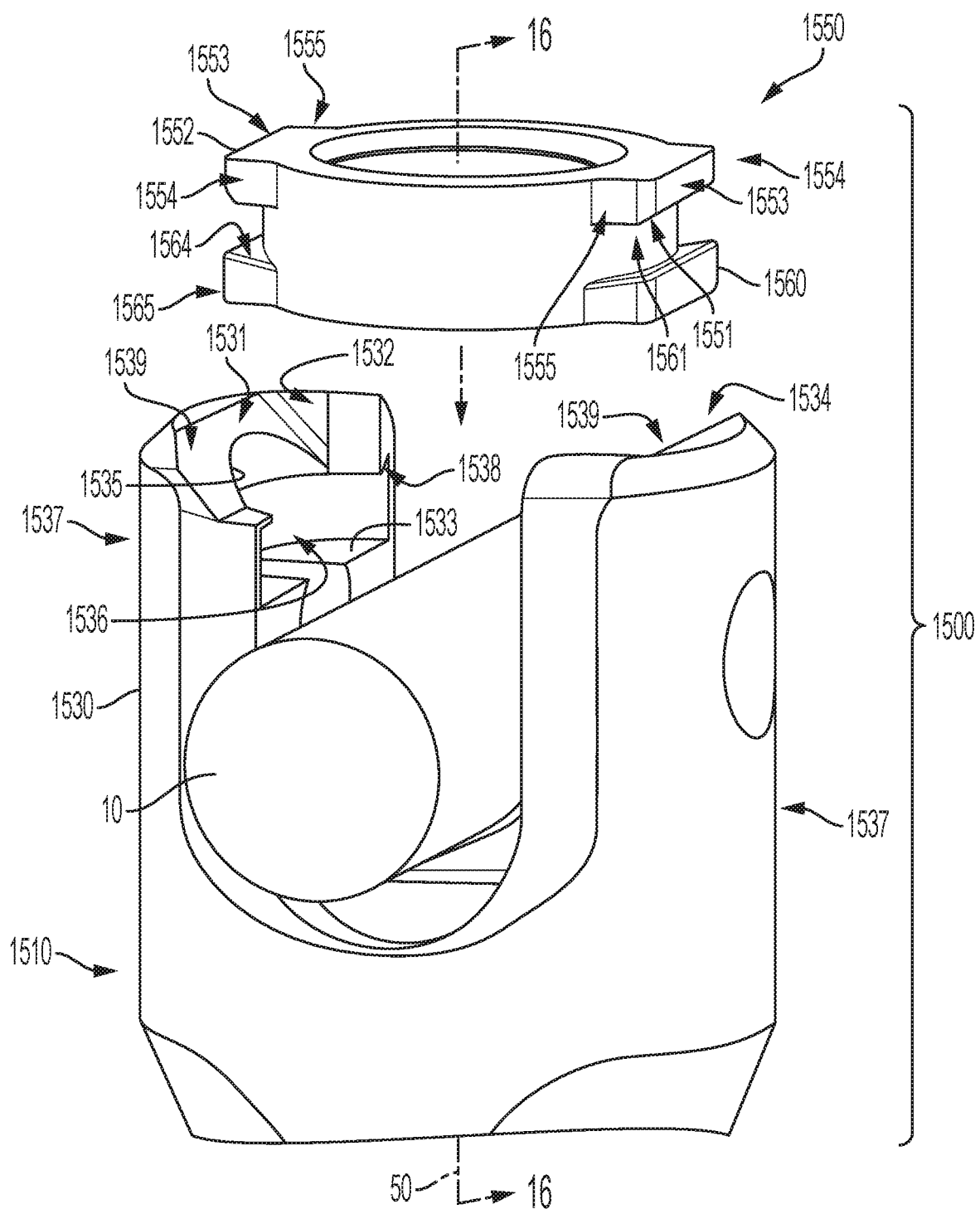
FIG. 15 is a perspective view of a cap and receiver, prior to popping the cap onto the receiver, according to a fourth embodiment of the present technology.
Figure 16:
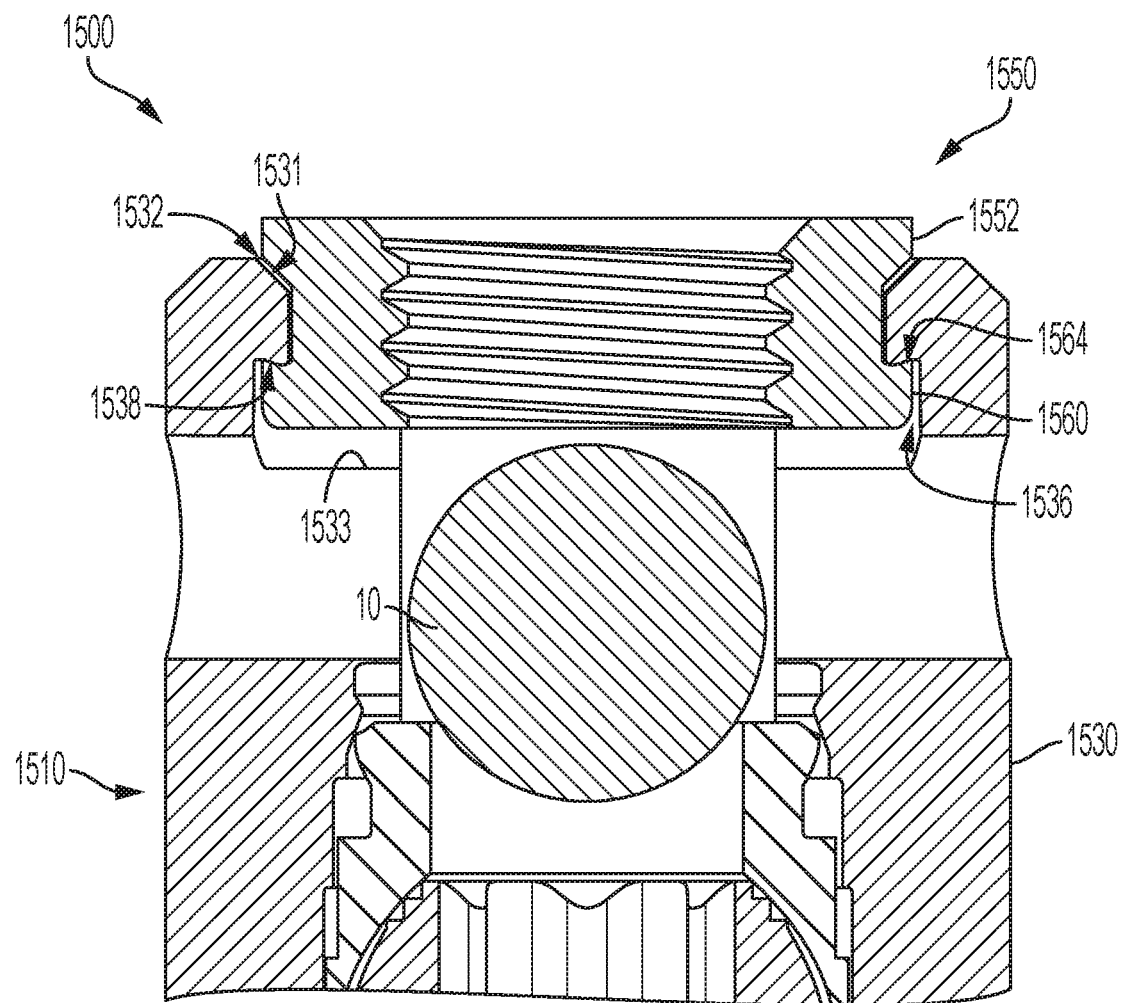
FIG. 16 is a side cross section of the system of the fourth embodiment, taken alone line 16-16 of FIG. 15, with the cap having been popped onto the receiver.
Figure 17:
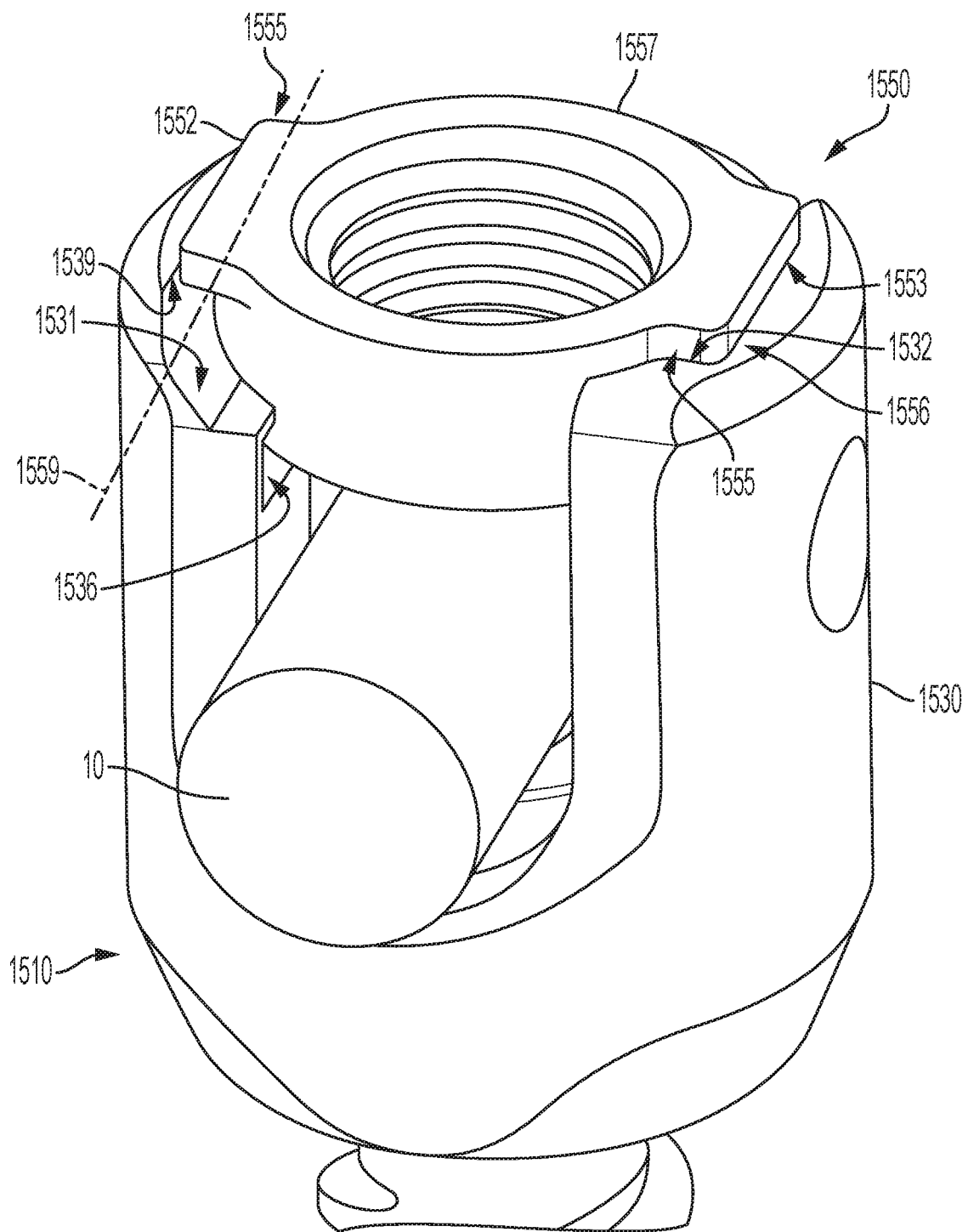
FIG. 17 is a perspective view of the embodiment and state of FIG. 16.

Turning to the fourth main related embodiment, FIGS. 15-17 show a system 1500 again having a pop-on cap 1550 and receiver 1510. The fourth embodiment is in many ways like the third embodiment. One of the primary distinctions is that interfacing features of the cap and receiver for rotation-prevention and rotation-resistance for the cap are configured differently than those of the third embodiment.

FIG. 15 is a perspective view of the cap 1550 and receiver 1510, prior to popping the cap onto the receiver, according to a fourth embodiment of the present technology.

For initially securing the cap 1550 to the receiver 1510, the cap 1550 is lowered toward the receiver 1510 along a system axis 50, as indicated by arrow. The cap 1550 is orientated for the maneuver with rotation-resisting/rotation-preventing wings 1552 aligned, or positioned, over wing-receiving spaces, or gaps, 1534 of the receiver 1510, and/or with distal pop-on/splay-resisting flanges 1560 aligned over the spaces 1534. The cap 1550 is popped onto the receiver 1510 in a manner similar to the pop-on maneuver described above in connection with the embodiments of FIGS. 2-7.

The cap 1550 and receiver 1510 are further configured (e.g., sized and shaped) such that splaying of the receiver arms 1530 is resisted, in a manner similar to how splaying of the receiver 110 is resisted after cap 150 installation was described in connection with the embodiments of FIGS. 1-9 and 10.

The rotation-resisting/rotation-preventing cap wings 1552 in various embodiments have a generally rectangular profile, as shown in FIG. 15. The shape can include a lateral surface 1553 and opposing side surfaces 1554, for instance. One of each set of side surfaces 1554 is anti-rotation surface 1555. The cap anti-rotation surfaces 1555 abut anti-rotation surfaces 1532 of the receiver, preventing rotation of the cap in a first direction, e.g., clockwise looking distally. In various embodiments, the end surfaces 1555, though, additional surfaces of the wings 1552 act to prevent rotation. For instance, the lateral surface 1553 of each wing 1552 can contact the opposing surface 1539 of the receiver, further preventing rotation of the cap in the receiver. In some cases, most, or generally all of the length of the lateral surface 1553 can contact the opposing surface 1539 of the receiver, further preventing rotation. A portion of the lateral surface 1553 adjacent or closest to the interface to the end surface 1555, and adjacent portion of the receiver surface 1539, are in various embodiments where a majority of the rotation-prevention force is focused.

Each cap wing 1552 can also include a sloped or angled distal surface 1551. The surface 1551 extends at an angle with respect to an external side wall 1561 of the cap body of between about 40 and about 50 degrees, in various embodiments. The angle may be generally 45 degrees, for instance.

The angle in some cases corresponds, such as by being the same or about the same as, to an angle at which a receiver proximal pop-on surface 1531 extends with respect to an exterior side wall 1537 of the receiver 1510. The corresponding angulation allows the angled distal surface 1551 of the cap 1550 to sit more robustly, such as flush or generally flush, with the angled proximal surface 1531, which provides a more-secure seating of the wings 1552, and so the cap 1550, against the proximal receiver surface 1531, and so against the receiver 1510. An angled distal wing surface 1551 also allows the cap 1550 to be lowered farther into the receiver 1510 than the cap would be able to go distally if the lower outer edge of the wings were square, or more square.

Each cap distal pop-on/splay-resisting flange 1560, and corresponding receiver features, can be configured in any of the ways that pop-on/splay-resisting flanges, and corresponding receiver features, were configured in the embodiments of FIGS. 1-14, such as cap flanges 160 of FIGS. 1-9. Each flange 1560 can have an angled proximally facing splay-resisting surface 1564 corresponding to, for interfacing with, a distally facing receiver splay-resisting surface 1538, in the same way that the flange 160 has the proximally facing surface 164 corresponding for interface with the distally facing splay-resisting surface 138 described in connection with FIG. 2.

The receiver 1510 can further have a proximally facing flange-stop floor or surface 1533. When the cap 1550 is being popped onto the receiver 1510, distal surfaces of the cap flanges 1560 abut the stop surface 1533, preventing the cap 1550 from moving any farther distally in the receiver 1510. The surface 1433 can in any way be like the surface 133 described in connection with the embodiment of FIG. 2, and vice versa.

In various embodiments, the receiver 1510 has a cap-body receiving cavity 1535. The cavity 1535 allows the cap 1550 to be moved farther distally in the receiver 1510, as, if the pop-on surface 1531 was continuous, without the cavity 1535 cutout, the side wall 1561 of the cap 1550 would contact the (hypothetical) continuous surface 1531, keeping the cap from moving further distally in the receiver 1510.

The receiver 1510 further includes a cap-flange-receiving cavity 1536. The cavity 1536 can in any way be like the cavity 136 described in connection with the embodiment of FIG. 2.

As the cap pop-on surfaces 1565 contact and then are pushed farther distally against the receiver pop-on surfaces 1531, the cap surfaces 1565 slide distally along the receiver surfaces 1531. In this, the receiver arms 1530 are forced to splay slightly, sufficiently to allow the cap flanges 1560 to pass the slope 1531. As the flanges clear the slope 1531, contact between the flanges 1560 and slope 1531 is released, and the flanges 1560 enter the receiver cap-receiving cavities 1536 as the receiver arms 1530 return from being splayed, by natural spring back of the arms 1530.

FIG. 16 is a side cross section of the system 1550 of the fourth embodiment, taken alone line 16-16 of FIG. 15. The view shows the cap 1550 having been popped onto the receiver 1510. For the popping on, between the view of FIGS. 15 and 16, a cap pop-on surface 1565, such as a distal/lateral edge or surface, pushes against the receiver pop-on surface 1531 as the cap 1550 is lowered into contact with the receiver, and then pushed further distally with respect to the receiver. The cap pop-on surface 1565 can in any way be like the cap pop-on surface 162 described above in connection with FIG. 2, including angulation (angle 165) of the surface 1565. Likewise, the receiver pop-on surface 1531 can in any way be like the receiver pop-on surface 134 described above in connection with the embodiment of FIG. 2, including angulation (angle 115) of the surface 132.

When the cap 1550 is popped into the receiver 1510, as shown in FIGS. 16 and 17, the cap cannot be turned in a first direction, e.g., clockwise looking down in FIG. 17. The first-direction rotation is prevented by interface between the cap anti-rotation surface 1555 and the receiver anti-rotation surface 1532. For instance, when the cap 1550 is installed, as shown, and a user threads a setscrew in the first direction into the cap 1550, interface between the anti-rotation surfaces 1555, 1532 abut to keep the cap 1550 from rotating in the same direction with respect to the receiver 1510. This facilitated setscrew installation. A setscrew is not shown in FIGS. 15-17 for this embodiment, but, again, is shown by way of example in FIGS. 12-14 by reference numeral 20.

When the cap 1550 is popped into the receiver 1510, as shown in FIGS. 16 and 17, the splay-resisting surfaces 1564, 1538 of the cap and receiver interface to prevent splaying absent sufficient splaying force applied to the receiver arms 1530. The sufficient splaying force is applied by turning the cap in the second direction, e.g., counterclockwise looking distally.

Each of the receiver and cap anti-rotation surfaces 1555, 1532 may extend generally orthogonal to a tangent 1559 of a generally cylindrical body 1557 of the cap 1550.

The cap wing 1552 and proximal arm 1530 features, including the wing-receiving space 1532, are configured (e.g., sized, shaped, and oriented) such that upon application of at least the predetermined amount of torque to the cap 1550 in the second direction, the cap 1550 rotates in the second direction with respect to the receiver 1510. In this cap rotation, a rotation-resisting portion 1556 of the cap 1550 sliding along the rotation-resisting surface 1136 of the receiver 1510. The rotation-resisting portion 1556 includes a rotation-resisting surface, toward an end of the lateral surface 1553 of the wing 1552, in the area indicated by reference numeral 1556.

Torque can be applied to the cap 1550 in any of a variety of ways to force intentional splay of the arms 1530. The system 1500 can include or be used with an instrument or tool (not shown) configured at its distal end to engage a proximal portion of the wings 1552, for instance, and configured to apply at least said pre-determined amount of torque to the cap 1550 in the second direction (e.g., counterclockwise), the force being sufficient to overcome friction between the rotation-resisting surfaces 1556, 1539. The cap surface 1556 can thereby slide with respect to the receiver surface 1539, as described, enabling the cap 1550 to rotate with respect to receiver 1510, thereby splaying the arms 1530 for cap removal.

As can be seen in FIGS. 16 and 17, the proximal surface of the wings 1552 can extend higher (farther proximally) than an adjacent proximal surface of the receiver arms 1530. The exposed proximal portion of the cap wings 1552 provides real estate that the instrument can interface with to apply torque to the cap 1550 in the second direction. The instrument can apply torque against the portion of the anti-rotation surfaces 1555 of the wings 1552 extending above the arms 1530, for instance.

A component of forces that the cap rotation-resisting surfaces or portions 1556 apply to adjacent receiver rotation-resisting surfaces 1539, sliding in the second direction (e.g., counterclockwise) along the receiver rotation-resisting surfaces 1539, is a radial force. As the radial force is applied to the receiver rotation-resisting surfaces 1539, and thereby to the receiver arms 1530, the arms 1530 are intentionally splayed.

As the receiver arms 1530 of this embodiment are splayed intentionally, the splay-resisting interfaces 1538, 1564 are pushed apart, namely the receiver splay-resisting surfaces 1538 are forced to move radially outward, along and then off of the cap splay-resisting surface 1564. The cap 1550 is then free from the receiver 1510, and can be removed in the proximal direction from the receiver 1510. In various embodiments, the splaying instrument has a capture design for grasping, engaging, or otherwise persuading the cap 1550 to move proximally, out of the receiver 1510, while the arms 1530 are splayed by the instrument. Or a separate cap removing instrument, such as one that can fit within, around, or aside of the splaying instrument, can persuade the cap 1550 proximally out of the receiver 1510 while the arms 1530 are splayed. Such removing feature or instrument can have an external thread, for instance, for engaging with the internal thread of the cap 1550.

It should be understood that various aspects disclosed herein may be combined in combinations other than the combinations presented specifically in the description and the accompanying drawings. It should also be understood that, depending on the example, certain acts or events of any of the processes or methods described herein may be performed in other sequence, added, merged, or left out altogether (e.g., all described acts or events may not be necessary to carry out the techniques).

In addition, while certain aspects of this disclosure are described as being performed by a single module or unit for purposes of clarity, it should be understood that the techniques of this disclosure may be performed by a combination of units or modules associated with, for example, a medical device.

Unless defined specifically otherwise herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an," and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed:

1. A system for use in spinal surgery, comprising:
   a cap having a generally cylindrical body defining a first longitudinal axis, a set of opposing splay-resisting flanges extending radially from the body, and a set of opposing rotation-preventing/rotation-resisting wings extending radially from the body, each cap wing having a lateral rotation-preventing portion, a lateral rotation-resisting portion and a distal surface extending at an acute angle relative to the first longitudinal axis; and
   a receiver having opposing arms spaced equally from a second longitudinal axis of the receiver, each arm extending to a respective proximal end from a common distal base and having an inner proximal protrusion at or adjacent the proximal end, the proximal end forming a wing-receiving cavity having a lateral rotation-preventing side and a lateral rotation-resisting side;
   wherein:
   each cap flange has a proximal-facing splay-resist surface, sloped proximally and radially outward, and a distal-facing pop-on surface;
   each receiver proximal protrusion has (i) a proximal-facing sloped receiver pop-on surface each configured to engage one of the distal surfaces of one of the wings and extending distally and radially inward toward the second longitudinal axis, and (ii) a distal-facing sloped receiver splay-resist surface extending distally and radially inward toward the second longitudinal axis;
   each rotation-preventing portion of the cap wing is configured to contact a corresponding one of the rotation-preventing side of the wing-receiving cavity and each rotation-resisting portion of the cap wing is configured to contact a corresponding one of the rotation-resisting sides of the wing-receiving cavity when the cap is popped onto the receiver;
   the rotation-preventing portions of the cap wing and rotation-preventing sides of the wing-receiving cavity are configured such that when the cap is installed onto the receiver, the rotation-preventing portions and the rotation-preventing sides prevent cap rotation in a first direction;
   the rotation-resisting portion of the cap wing and rotation-resisting side of the wing-receiving cavity are configured such that when the cap is installed onto the receiver, the rotation-resisting portion and the rotation-resisting sides resist cap rotation in a second direction, opposite the first direction; and
   the rotation-resisting portion of the cap wing is configured to splay the arms of the receiver and allow cap rotation in the second direction in response to a threshold torque being applied to the cap in the second direction.

2. The system of claim 1, wherein each rotation-preventing/rotation-resisting wing has a generally rectangular profile, looking distally at the cap.

3. The system of claim 1, wherein each rotation-preventing/rotation-resisting wing has opposing wing sides, each side extending from the body at a wing-cap interface generally orthogonally to a tangent of the body at or adjacent the interface.

4. The system of claim 1, wherein:
   each cap rotation-preventing portion comprises a rotation-resisting portion extending from the cap body at a wing base; and
   each cap rotation-preventing portion extends from the wing base at an angle, with respect to a body tangent contacting an edge of the wing base, of between about 80 degrees and about 100 degrees.

5. The system of claim 1, wherein:
   each cap rotation-preventing portion comprises a rotation-resisting portion extending from the cap body at a wing base; and
   each cap rotation-resisting portion extends from the wing base at an angle, with respect to a body tangent contacting an edge of the wing base, of between about 80 degrees and about 100 degrees.

6. The system of claim 1, wherein each arm has a curved rim, and each receiver rotation-preventing side extends at an angle, with respect to respective a rim tangent, of between about 80 degrees and about 100 degrees.

7. The system of claim 1, wherein the flanges are distal to the wings.

8. The system of claim 1, wherein:
   the flanges extend from the body along a first radial line of the body, and
   the wings extend radially from the body along a second radial line of the body generally parallel to the first radial line.

9. The system of claim 1, wherein:
   proximal surfaces of the cap wings lie on a first plane; and
   proximal surfaces of the receiver arms lie on a second plane distal to the first plane when the cap is popped onto the receiver.

10. The system of claim 1, wherein the receiver pop-on surfaces are spaced from each other such that each cap pop-on surface contacts a respective one of the receiver pop-on surfaces when the cap is centered on the second longitudinal axis, with the cap wings aligned over the wing-receiving cavities, and moved distally to contact the receiver.

11. The system of claim 1, wherein each receiver pop-on surface extends at a receiver pop-on angle with respect to a horizontal reference frame of between about 50 degrees and about 80 degrees.

12. The system of claim 1, wherein:
   each receiver arm has an inner surface extending from a distal portion to a proximal portion adjacent said proximal end of the arm; and
   the proximal portion of each inner surface defines a protrusion cavity configured to receive the cap flange when the cap is popped onto the receiver.

13. The system of claim 1, wherein:
the proximal end of each receiver arm has opposing side areas;
each cap wing extends between a first side end and a second side end;
the rotation-preventing portion of each cap wing is at the first side end of the cap wing;
a first side area of the opposing receiver-arm side areas comprises the rotation-preventing side of the receiver, for abutting the rotation-preventing portion of the cap wing when the cap is installed into the receiver, preventing relative rotation of the cap in the first direction with respect to the receiver when the cap is installed into the receiver; and
a second side area of the opposing receiver-arm side areas is generally open, such that the cap wing is not impeded from rotating in the second direction at the second side area on a second side of the wing when the cap is installed into the receiver.

14. A system for use in spinal surgery, comprising:
a cap configured to be popped into a rod receiver, the cap having a generally cylindrical body defining a first longitudinal axis, a set of opposing splay-resisting flanges extending radially from the body, and a set of opposing rotation-preventing/rotation-resisting wings extending radially from the body, each cap wing having a lateral rotation-preventing portion, a lateral rotation-resisting portion and a distal surface extending at an acute angle relative to the first longitudinal axis;
the receiver having opposing arms spaced equally from a second longitudinal axis of the receiver, each arm extending to a respective proximal end from a common distal base and having an inner proximal protrusion at or adjacent the proximal end, the proximal end forming a wing-receiving cavity having a lateral rotation-preventing side and a lateral rotation-resisting side, each receiver proximal protrusion having (i) a proximal-facing sloped receiver pop-on surface each configured to engage one of the distal surfaces of one of the wings and extending distally and radially inward toward the second longitudinal axis, and (ii) a distal-facing sloped receiver splay-resist surface extending distally and radially inward toward the second longitudinal axis;
wherein:
each rotation-preventing portion of the cap wing is configured to contact a corresponding one of the rotation-preventing side of the wing-receiving cavity to prevent cap rotation in a first direction;
each rotation-resisting portion of the cap wing is configured to contact a corresponding one of the rotation-resisting sides of the wing-receiving cavity to resist cap rotation in a second direction, opposite the first direction; and
the rotation-resisting portion of the cap wing is further configured to splay the arms of the cap in response to application of a threshold torque.

15. The system of claim 14, wherein each rotation-preventing/rotation-resisting wing has a generally rectangular profile, looking distally at the cap.

16. The system of claim 14, wherein each rotation-preventing/rotation-resisting wing has opposing wing sides, each side extending from the body at a wing-cap interface generally orthogonally to a tangent of the body at or adjacent the interface.

17. The system of claim 14, wherein:
each cap rotation-preventing portion comprises a rotation-resisting portion extending from the cap body at a wing base; and
each cap rotation-preventing portion extends from the wing base at an angle, with respect to a body tangent contacting an edge of the wing base, of between about 80 degrees and about 100 degrees.

18. The system of claim 14, wherein:
each cap rotation-preventing portion comprises a rotation-resisting portion extending from the cap body at a wing base; and
each cap rotation-resisting portion extends from the wing base at an angle, with respect to a body tangent contacting an edge of the wing base, of between about 80 degrees and about 100 degrees.

19. The system of claim 14, wherein each arm has a curved rim, and each receiver rotation-preventing side extends at an angle, with respect to respective a rim tangent, of between about 80 degrees and about 100 degrees.

20. The system of claim 14, wherein the flanges are distal to the wings.

21. The system of claim 14, wherein:
the flanges extend from the body along a first radial line of the body, and
the wings extend radially from the body along a second radial line of the body generally parallel to the first radial line.

22. The system of claim 14, wherein:
proximal surfaces of the cap wings lie on a first plane; and
proximal surfaces of the receiver arms lie on a second plane distal to the first plane when the cap is popped onto the receiver.

23. A system for use in spinal surgery, comprising:
a receiver configured to receive a pop-on cap, the receiver having opposing arms spaced equally from a first longitudinal axis of the receiver, each arm extending to a respective proximal end from a common distal base and having an inner proximal protrusion at or adjacent the proximal end, the proximal end forming a wing-receiving cavity having a lateral rotation-preventing side and a lateral rotation-resisting side, the protrusions each having an angled proximal surface;
the cap having a generally cylindrical body defining a second longitudinal axis, a set of opposing splay-resisting flanges extending radially from the body, and a set of opposing rotation-preventing/rotation-resisting wings extending radially from the body, each cap wing having a lateral rotation-preventing portion, a lateral rotation-resisting portion, and a distal surface extending at an acute angle relative to the second longitudinal axis, each distal surface configured to engage corresponding angled proximal surfaces of one of the protrusions,
wherein:
each rotation-preventing portion is configured to contact a corresponding one of the rotation-preventing sides to prevent cap rotation in a first direction;
each rotation-resisting portion is configured to contact a corresponding one of the rotation-resisting sides to resist cap rotation in a second direction, opposite the first direction, wherein each rotation-resisting portion is further configured to splay the arms of the receiver to allow cap rotation in the second direction in response to a threshold torque being applied to the cap in the second direction.

24. The system of claim 23, wherein each arm has a curved rim, and each receiver rotation-preventing side extends at an angle, with respect to a respective rim tangent, of between about 80 degrees and about 100 degrees.

25. The system of claim 23, wherein:
the proximal end of each receiver arm has opposing or adjacent side areas;
each cap wing extends between a first side end and a second side end;
the rotation-preventing portion of each cap wing is at the first side end of the cap wing,
a first side area of the opposing receiver-arm side areas comprises the rotation-preventing side of the receiver, for abutting the rotation-preventing portion of the cap wing when the cap is installed into the receiver, preventing relative rotation of the cap in the first direction with respect to the receiver when the cap is installed into the receiver; and
a second side area of the opposing receiver-arm side areas is generally open, such that the cap wing is not impeded from rotating in the second direction at the second side area on a second side of the wing when the cap is installed into the receiver.

26. The system of claim 23, wherein the receiver pop-on surfaces are spaced from each other such that each cap pop-on surface contacts a respective one of the receiver pop-on surfaces when the cap is centered on the first longitudinal axis, with the cap wings aligned over the wing-receiving cavities, and moved distally to contact the receiver.

27. The system of claim 23, wherein each receiver pop-on surface extends at a receiver pop-on angle with respect to a horizontal reference frame of between about 50 degrees and about 80 degrees.

28. The system of claim 23, wherein:
each receiver arm has an inner surface extending from a distal portion to a proximal portion adjacent said proximal end of the arm; and
the proximal portion of each inner surface defines a protrusion cavity configured to receive the cap flange when the cap is popped onto the receiver.

* * * * *